United States Patent
Dotti et al.

(10) Patent No.: US 11,725,061 B2
(45) Date of Patent: Aug. 15, 2023

(54) CSGP4—SPECIFIC CHIMERIC ANTIGEN RECEPTOR FOR CANCER

(71) Applicants: Baylor College of Medicine, Houston, TX (US); The General Hospital Corporation, Boston, MA (US)

(72) Inventors: Gianpietro Dotti, Chapel Hill, NC (US); Soldano Ferrone, Boston, MA (US)

(73) Assignees: The General Hospital Corporation, Boston, MA (US); Baylor College of Medicine, Houston, TX (US)

( * ) Notice: Subject to any disclaimer, the term of this patent is extended or adjusted under 35 U.S.C. 154(b) by 359 days.

(21) Appl. No.: 15/965,333

(22) Filed: Apr. 27, 2018

(65) Prior Publication Data
US 2018/0251568 A1  Sep. 6, 2018

Related U.S. Application Data

(63) Continuation of application No. 15/038,997, filed as application No. PCT/US2014/066953 on Nov. 21, 2014, now abandoned.

(60) Provisional application No. 61/909,788, filed on Nov. 27, 2013.

(51) Int. Cl.
| | |
|---|---|
| *C07K 16/30* | (2006.01) |
| *A61K 35/17* | (2015.01) |
| *C07K 14/705* | (2006.01) |
| *C07K 14/725* | (2006.01) |
| *A61K 39/00* | (2006.01) |

(52) U.S. Cl.
CPC .......... *C07K 16/3076* (2013.01); *A61K 35/17* (2013.01); *C07K 14/7051* (2013.01); *C07K 14/70517* (2013.01); *C07K 14/70521* (2013.01); *C07K 14/70575* (2013.01); *C07K 14/70578* (2013.01); *C07K 14/70596* (2013.01); *C07K 16/30* (2013.01); *A61K 2039/505* (2013.01); *C07K 2317/53* (2013.01); *C07K 2317/622* (2013.01); *C07K 2319/01* (2013.01); *C07K 2319/03* (2013.01); *C07K 2319/30* (2013.01)

(58) Field of Classification Search
None
See application file for complete search history.

(56) References Cited

U.S. PATENT DOCUMENTS

| | | | |
|---|---|---|---|
| 7,361,342 B2 | 4/2008 | Young et al. | |
| 7,393,531 B2 | 7/2008 | Young et al. | |
| 7,550,568 B2 | 6/2009 | Ferrone | |
| 7,939,531 B2 | 5/2011 | Bamberg et al. | |
| 8,318,162 B2 | 11/2012 | Horwitz | |
| 8,318,165 B2 | 11/2012 | Keler et al. | |
| 8,476,410 B2 | 7/2013 | Wang et al. | |
| 8,486,393 B2 | 7/2013 | Ferrone et al. | |
| 11,091,547 B2 | 8/2021 | Ferrone et al. | |
| 2013/0007825 A1 | 1/2013 | Liu et al. | |
| 2013/0078251 A1* | 3/2013 | Freytag ............... | C07K 16/18 424/137.1 |
| 2014/0242079 A1 | 8/2014 | Bacac et al. | |
| 2014/0248290 A1 | 9/2014 | Karbassi et al. | |
| 2016/0024175 A1* | 1/2016 | Chow ............... | A61K 38/1774 424/278.1 |
| 2017/0342151 A1 | 11/2017 | Ferrone et al. | |

FOREIGN PATENT DOCUMENTS

| | | |
|---|---|---|
| WO | 2013/074916 A1 | 5/2013 |
| WO | WO-2016/077638 A1 | 5/2016 |

OTHER PUBLICATIONS

ASGCT 16th Annual Meeting Abstracts, Molecular Therapy, May 15, 2013 (May 15, 2013), pp. SI-S258.
Schmidt et al., "Eradication of melanomas by targeted elimination of a minor subset of tumor cells", Proceedings of the National Academy of Sciences, vol. 108, No. 6, Feb. 8, 2011 (Feb. 8, 2011), pp. 2474-2479.
Burns et al., "A High Molecular Weight Melanoma-Associated Antigen-Specific Chimeric Antigen Receptor Redirects Lymphocytes to Target Human Melanomas", Cancer Research, vol. 70, No. 8, Apr. 15, 2010 (Apr. 15, 2010), pp. 3027-3033.
Geiser et al., "Identification of the human melanoma-associated chondroitin sulfate proteoglycan antigen epitope recognized by the antitumor monoclonal antibody 763.74 from a peptide phage library", Cancer Research, American Association for Cancer Research, US, vol. 59, No. 4, Feb. 15, 1999 (Feb. 15, 1999), pp. 905-910.
Geldres et al., "T Lymphocytes Redirected against the Chondroitin Sulfate Proteoglycan-4 Control the Growth of Multiple Solid Tumors both In Vitro and In Vivo", Clinical Cancer Research, vol. 20, No. 4, Dec. 13, 2013 (Dec. 13, 2013), pp. 962-971.
Rettig et al. (J. Immunology 2009 182: 121-129) (Year: 2009).
Vera et al. (Blood Dec. 1, 2006 108 (12) 3890-3897) (Year: 2006).
Zhao et al. (J. Immunology 2009 183:5563-5574) (Year: 2009).
Tannock, I.F. (Experimental Chemotherapy, Ch. 19-p. 338 and 352-359, in the Basic Science of Oncology Tannock and Hill, eds., New York 1992) (Year: 1992).
Reinhold et al. (J.Investigative Dermatology 1999 112: 744-750), (Year: 1999).

(Continued)

*Primary Examiner* — Peter J Reddig
(74) *Attorney, Agent, or Firm* — Clark & Elbing LLP

(57) ABSTRACT

Embodiments of the disclosure include methods and compositions related to chimeric antigen receptors (CAR) that target chondroitin sulfate proteoglycan-4 (CSPG4). T cells transduced with a CSPG4-specific CAR are effective for inhibition of particular cancer cells that express CSPG4. In certain embodiments, the cancer is melanoma, breast cancer, head and neck cancer, mesothelioma, glioblastoma, or renal cancer.

18 Claims, 31 Drawing Sheets

Specification includes a Sequence Listing.

(56) References Cited

OTHER PUBLICATIONS

Pellegatta et al., "Constitutive and TNFα-inducible expression of chondroitin sulfate proteoglycan 4 in glioblastoma and neurospheres: Implications for CAR-T cell therapy," Sci Transl Med. 10(430):eaao2731 (2018) (46 pages, supplementary materials included).

* cited by examiner

A

Endometrium
 Lung
 Skeletal muscle
 Nerve
 Skin
 Lung carcinoma

SEQUENCE LISTING

<160> NUMBER OF SEQ ID NOS: 2

<210> SEQ ID NO 1
<211> LENGTH: 777
<212> TYPE: DNA
<213> ORGANISM: Artificial Sequence
<220> FEATURE:
<223> OTHER INFORMATION: Synthetic Primer

<400> SEQUENCE: 1

```
atggagtttg gctgagctg gcttttct gtggctattt taaaaggtgt ccagtgctct      60
agaatggccc aggtcaaact gaaggagtct ggacctgagc tgaagaagcc tggagagaca     120
gtcaagatct cctgcaaggc ttctggttat accttcacag actattcaat gcactgggtg     180
aagaagactc caggaaaggg tttaaagtgg ctgggctgga taaacactgc gactggtgag     240
ccaacatatg cagatgactt caagggacgg tttgccatct ctttggaaac ctctgccagg     300
actgtctatt tgcagatcaa taatctcaga aatgaggaca cggctacata tttctgtttt     360
agttactacg actactgggg ccaaggcacc acggtcaccg tctcctcagg tggggcggt      420 tcaggcggag gtggctctgg cggtggcgga ttggacatca agctcactca gtctccatcc     480
atcctgtctg tgactccagg tgaaacagtc agtctttcct gtagggccag ccagactatt     540
tacaagaacc tacactggta tcaacagaaa tcacatcggt ctccaaggct tctcatcaag     600
tatggttctg attccatctc tgggatcccc tccaggttca ctgcagtgg atcagggaca     660 gattacactc tcaatatcaa cagtgtgaag cccgaagatg aaggaatata ttactgtctt     720
caaggttaca gtacaccttg gacgttcggt ggagggacca agctggaaat aaaacgg       777
```

<210> SEQ ID NO 2
<211> LENGTH: 259
<212> TYPE: PRT
<213> ORGANISM: Artificial Sequence
<220> FEATURE:
<223> OTHER INFORMATION: Synthetic Peptide

<400> SEQUENCE: 2

```
Met Glu Phe Gly Leu Ser Trp Leu Phe Leu Val Ala Ile Leu Lys Gly
1               5                   10                  15

Val Gln Cys Ser Arg Met Ala Gln Val Lys Leu Lys Glu Ser Gly Pro
            20                  25                  30

Glu Leu Lys Lys Pro Gly Glu Thr Val Lys Ile Ser Cys Lys Ala Ser
        35                  40                  45

Gly Tyr Thr Phe Thr Asp Tyr Ser Met His Trp Val Lys Lys Thr Pro
    50                  55                  60

Gly Lys Gly Leu Lys Trp Leu Gly Trp Ile Asn Thr Ala Thr Gly Glu
65                  70                  75                  80

Pro Thr Tyr Ala Asp Asp Phe Lys Gly Arg Phe Ala Ile Ser Leu Glu
                85                  90                  95
```

```
Thr Ser Ala Arg Thr Val Tyr Leu Gln Ile Asn Asn Leu Arg Asn Glu
            100                 105                 110
Asp Thr Ala Thr Tyr Phe Cys Phe Ser Tyr Tyr Asp Tyr Trp Gly Gln
            115                 120                 125
Gly Thr Thr Val Thr Val Ser Ser Gly Gly Gly Ser Gly Gly Gly
            130                 135                 140
Gly Ser Gly Gly Gly Gly Leu Asp Ile Lys Leu Thr Gln Ser Pro Ser
145                 150                 155                 160
Ile Leu Ser Val Thr Pro Gly Glu Thr Val Ser Leu Ser Cys Arg Ala
            165                 170                 175
Ser Gln Thr Ile Tyr Lys Asn Leu His Trp Tyr Gln Gln Lys Ser His
            180                 185                 190
Arg Ser Pro Arg Leu Leu Ile Lys Tyr Gly Ser Asp Ser Ile Ser Gly
            195                 200                 205
Ile Pro Ser Arg Phe Thr Gly Ser Gly Ser Gly Thr Asp Tyr Thr Leu
            210                 215                 220
Asn Ile Asn Ser Val Lys Pro Glu Asp Glu Gly Ile Tyr Tyr Cys Leu
225                 230                 235                 240
Gln Gly Tyr Ser Thr Pro Trp Thr Phe Gly Gly Gly Thr Lys Leu Glu
            245                 250                 255
Ile Lys Arg
```

CSGP4—SPECIFIC CHIMERIC ANTIGEN RECEPTOR FOR CANCER

This application is a continuation of U.S. Non-Provisional application Ser. No. 15/038,997 filed May 24, 2016, which is a national phase application under 35 U.S.C. § 371 that claims priority to International Application No. PCT/US2014/066953 filed Nov. 21, 2014, which claims priority to U.S. Provisional Patent Application Ser. No. 61/909,788, filed Nov. 27, 2013, all of which are incorporated herein by reference in their entirety.

STATEMENT REGARDING FEDERALLY SPONSORED RESEARCH OR DEVELOPMENT

This invention was made with government support under P30 CA125123 awarded by the National Cancer Institute and under CA 138188 awarded by the National Institutes of Health. The government has certain rights in the invention.

SEQUENCE LISTING

The instant application contains a Sequence Listing which has been submitted electronically in ASCII format and is hereby incorporated by reference in its entirety. The ASCII copy, created on Oct. 8, 2020 is named 51412-004003 Sequence Listing 10.08.20 ST25 and is 3,834 bytes in size.

TECHNICAL FIELD

The fields of embodiments of the disclosure include at least cell biology, molecular biology, immunology, and medicine, including cancer medicine.

BACKGROUND

Chondroitin sulfate proteoglycan-4 (CSPG4), also known as high molecular weight-melanoma associated antigen (HMW) and melanoma-associated chondroitin sulfate proteoglycan (MCSP), is a well characterized cell surface proteoglycan first identified on human melanoma cells. Subsequent studies showed it to be highly expressed on other solid tumors such as mesothelioma and triple negative breast carcinoma, all of which often show an aggressive clinical course. In contrast, CSPG4 has a restricted distribution in normal tissues. CSPG4 participates in tumor migration, invasion, angiogenesis, and metastasis. It interacts with α4β1 integrins to directly modulate cell adhesion, motility and metastasis, as demonstrated by its ectopic expression in tumor cells. Given its restricted expression in normal tissues, high expression on various types of solid tumors and its role in the biology of tumor cells, CSPG4 is an attractive target for immunotherapy.

CSPG4 has been targeted with monoclonal antibodies (mAbs) in models of melanoma, mesothelioma, and breast carcinoma, resulting in the inhibition of tumor growth and survival in addition to thwarting the metastatic capability of tumor cells. Recent advances in potentiating the antitumor effects of a specific mAb rely on coupling its antigen-binding specificity with the effector function and long-term persistence of T lymphocytes to generate specific chimeric antigen receptors (CARs). These molecules are obtained by fusing the extracellular antigen-binding domain of the mAb with the intracellular signaling domains derived from the CD3-ζ chain of the T-cell receptor, in tandem to costimulatory endodomains to support survival and proliferative signals. Because CAR-modified T cells function independently of a patient's MHC and can readily be generated for clinical use, the targeting of CSPG4 with a CAR based-approach is useful.

The present embodiments provide a solution to a long-felt need in the art to provide effective methods and/or compositions for the treatment of particular cancers.

BRIEF SUMMARY

The present embodiments are directed to methods and/or compositions for the treatment of cancer. In particular cases, the disclosure concerns methods and/or compositions for the treatment of cancers in which the cancer cells comprise CSPG4 as a tumor antigen. Although in certain aspects the cancer may be of any kind, in particular cases the cancer is melanoma, breast cancer, head and neck cancer, mesothelioma, glioblastoma, or renal cancer. In specific embodiments, the cancer comprises solid tumors. In at least some cases, the cancer is not melanoma. In specific embodiments, the cancer is not breast cancer, such as not being triple negative breast cancer, for example. In a certain embodiment, the cancer is not ovarian cancer.

Embodiments of the disclosure encompass immune cells that express a CSPG4-targeting chimeric antigen receptor (CAR). In certain aspects, the CAR comprises a scFv specific for CSPG4. In specific embodiments, the scFv is not derived from the murine mAb 225.28S. In particular cases, the antibody is scFv 763.74 or any other commercially-available or otherwise available anti-CSPG4 antibodies. In certain embodiments, the antibody is not scFv 763.74 or is not derived from its respective monoclonal antibody. In particular embodiments, the CAR utilizes an scFv specific for CSPG4 that is known in the art, although in other embodiments, the CAR does not utilize an scFv specific for CSPG4 that is known in the art. In certain embodiments, the CAR utilizes an scFv specific for CSPG4 that is derived from a monoclonal antibody known in the art, whereas in other cases the CAR utilizes an scFv specific for CSPG4 that is not derived from a monoclonal antibody known in the art.

The CAR may include one or more costimulatory endodomains, such as CD28, CD27, 4-1BB, OX40, ICOS, or a combination thereof. The CAR may include one or more transmembrane domains, such as one selected from the group consisting of CD3-zeta, CD28, CD8α, CD4, or a combination thereof. In some embodiments, the immune cells are one of T cells, NK cells, dendritic cells, or a mixture thereof. In certain aspects, T cells redirected against CSPG4 control the growth of CSPG4-expressing cancers, either in vitro or in vivo, e.g., in an individual having a cancer comprising tumor cells that express CSPG4. The cells are effective against multiple solid tumors, in particular embodiments.

As described in detail herein, the expression of CSPG4 was validated in an extensive panel of tumor arrays and normal tissues and in gene expression profiling datasets. A CSPG4-specific CAR (referred to as CAR.CSPG4) was generated that showed that when it was expressed by T cells, melanoma was effectively targeted in vitro, and antitumor activity was observed in vitro and in vivo against many solid tumors including breast carcinoma, head and neck squamous cell carcinoma (HNSCC) and mesothelioma, for example. Redirecting T cells to CSPG4 using CARs thus represents a robust platform to target multiple types of solid tumors.

Because CSPG4 protein is expressed by several solid tumors including melanoma, breast cancer, HNSCC and mesothelioma, and because CSPG4 mRNA is detected in other tumors such as glioblastoma, renal cell carcinoma and at least some type of sarcomas, this antigen is an optimal target for adoptive T-cell immunotherapy based on CSPG4-CAR-redirected T cells. In addition, the lack of significant expression of CSPG4 in normal tissues further highlights its relevance for immunotherapy.

In one embodiment, there is a method of inhibiting proliferation of cancer cells, comprising the step of contacting the cancer cells with a therapeutically effective amount of immune cells that express a chimeric antigen receptor (CAR) that targets chondroitin sulfate proteoglycan-4 (CSPG4), wherein the cancer is not melanoma. In specific embodiments, the cancer is head and neck cancer, mesothelioma, breast cancer, glioblastoma, or renal cancer. The cancer may be a sarcoma. In some embodiments, the contacting is performed in vitro, in cell culture, or in vivo. In particular cases, the contacting is performed in vivo, and the immune cells are cells in an individual, such as T cells. In particular cases, the immune cells are autologous or allogeneic to the individual. In particular embodiments, the immune cells are T cells, NK cells, dendritic cells, or a mixture thereof. The T cells may be CD4+ T cells or CD8+ T cells or Treg cells. The immune cells may harbor a polynucleotide that encodes the CAR, and the polynucleotide may further comprise a suicide gene.

In some embodiments, the CAR comprises a transmembrane domain selected from the group consisting of CD3-zeta, CD28, CD8α, CD4, or a combination thereof. In particular embodiments, the CAR comprises a co-stimulatory molecule endodomain selected from the group consisting of CD28, CD27, 4-1BB, OX40 ICOS, and a combination thereof.

In specific methods of the disclosure, an individual subjected to the methods has received, is receiving, or will receive an additional cancer treatment, such as chemotherapy, immunotherapy, radiation, surgery, hormone therapy, or a combination thereof.

In one embodiment, there is a method of inhibiting proliferation of cancer cells, comprising the step of contacting the cancer cells with a therapeutically effective amount of immune cells that express a chimeric antigen receptor (CAR) that targets chondroitin sulfate proteoglycan-4 (CSPG4), wherein the CAR comprises a scFv antibody that is not derived from mAb 225.28S.

In a particular embodiment, there is a method of inhibiting proliferation of cancer cells, comprising the step of contacting the cancer cells with a therapeutically effective amount of immune cells that express a chimeric antigen receptor (CAR) that targets chondroitin sulfate proteoglycan-4 (CSPG4), wherein the CAR comprises a scFv 763.74 antibody.

In embodiments, one or more structural components of a CSPG4-specific CAR are contemplated herein. In specific embodiments, one can alter the length of the hinge between the $V_H$ and $V_L$ domains; short hinges and long hinges may be utilized. In specific embodiments, the hinge is between about 10 to 25 amino acids. In specific embodiments, a full hinge is employed. In certain embodiments, the hinge is rich in glycine, such as for flexibility, and/or is rich in serine and/or threonine, such as for solubility. In particular embodiments, the hinge can either connect the N-terminus of the $V_H$ with the C-terminus of the $V_L$, or vice versa. In certain embodiments, part or all of the hinge of IgG1 is employed. Optimization may occur in vitro and/or in vivo in NSG tumor-bearing mice, for example.

In some embodiments, one can optimize the transmembrane domain of the CAR. In specific embodiments, the transmembrane is derived from that of CD28 or. 4-1BB or CD8 alpha, for example. In other embodiment, one can optimize the number and kind of co-stimulatory endodomains; in specific cases, CD28 co-stimulatory endodomain, 4-1BB co-stimulatory endodomain, or both are employed.

Examples of certain combinations of structural components of a CSPG4-specific CAR are as follows: 1) full hinge of IgG1 and IgG1.$C_H2C_H3$ domain with CD28 transmembrane domain and CD28 or 4-1BB endodomains; 2) only hinge of IgG1 (in the absence of the IgG1$C_H2C_H3$ domain) with CD28 transmembrane domain and CD28 or 4-1BB endodomains; 3) only hinge of IgG1 (in the absence of the IgG1$C_H2C_H3$ domain) with CD8a alpha transmembrane domain and CD28 or 4-1BB endodomains; 4) full CD8a alpha stalk including hinge and transmembrane domain and CD28 or 4-1BB endodomains; and 5) all of these combinations plus CD28 and 4-1BB endodomains to make third generation CARs.

Additional features and advantages of the invention will be described hereinafter which form the subject of the claims of the invention. It should be appreciated by those skilled in the art that the conception and specific embodiment disclosed may be readily utilized as a basis for modifying or designing other structures for carrying out the same purposes of the present invention. It should also be realized by those skilled in the art that such equivalent constructions do not depart from the spirit and scope of the invention as set forth in the appended claims. The novel features which are believed to be characteristic of the invention, both as to its organization and method of operation, together with further objects and advantages will be better understood from the following description when considered in connection with the accompanying figures. It is to be expressly understood, however, that each of the figures is provided for the purpose of illustration and description only and is not intended as a definition of the limits of the present invention.

BRIEF DESCRIPTION OF THE DRAWINGS

For a more complete understanding of the present invention, reference is now made to the following descriptions taken in conjunction with the accompanying drawing, in which.

Panel B. Representative FACS analysis showing the expression of the CAR in CD3, CD4 and CD8 T cells after retroviral transduction. Panel C. Representative expression of the CD62L, CD45RO, and CCR7 markers on control and CAR.CSPG4+ T cells by flow cytometry on day 14 of culture. Numbers represent percentages of cells per quadrant.

Figure 3:
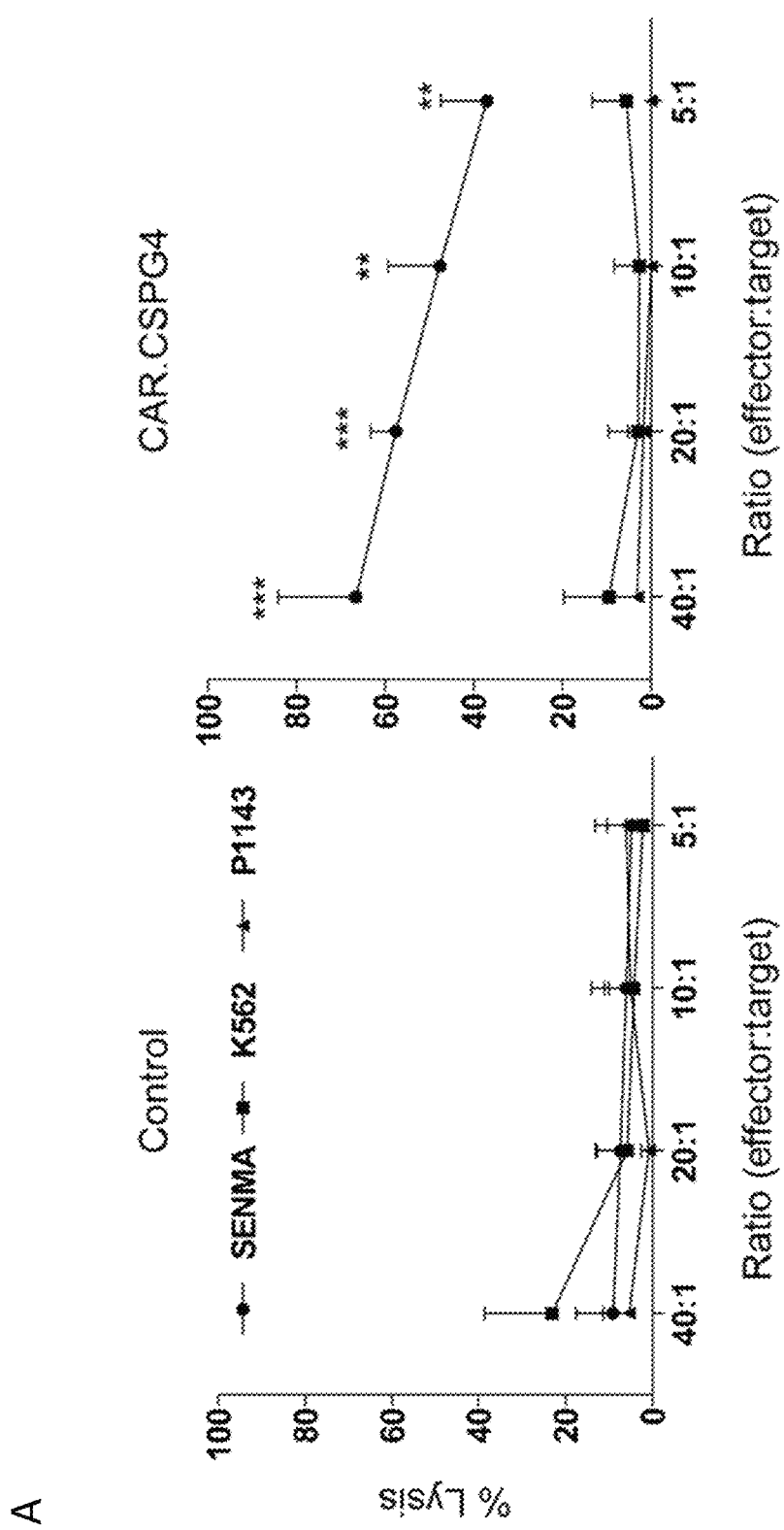
Figure 3:
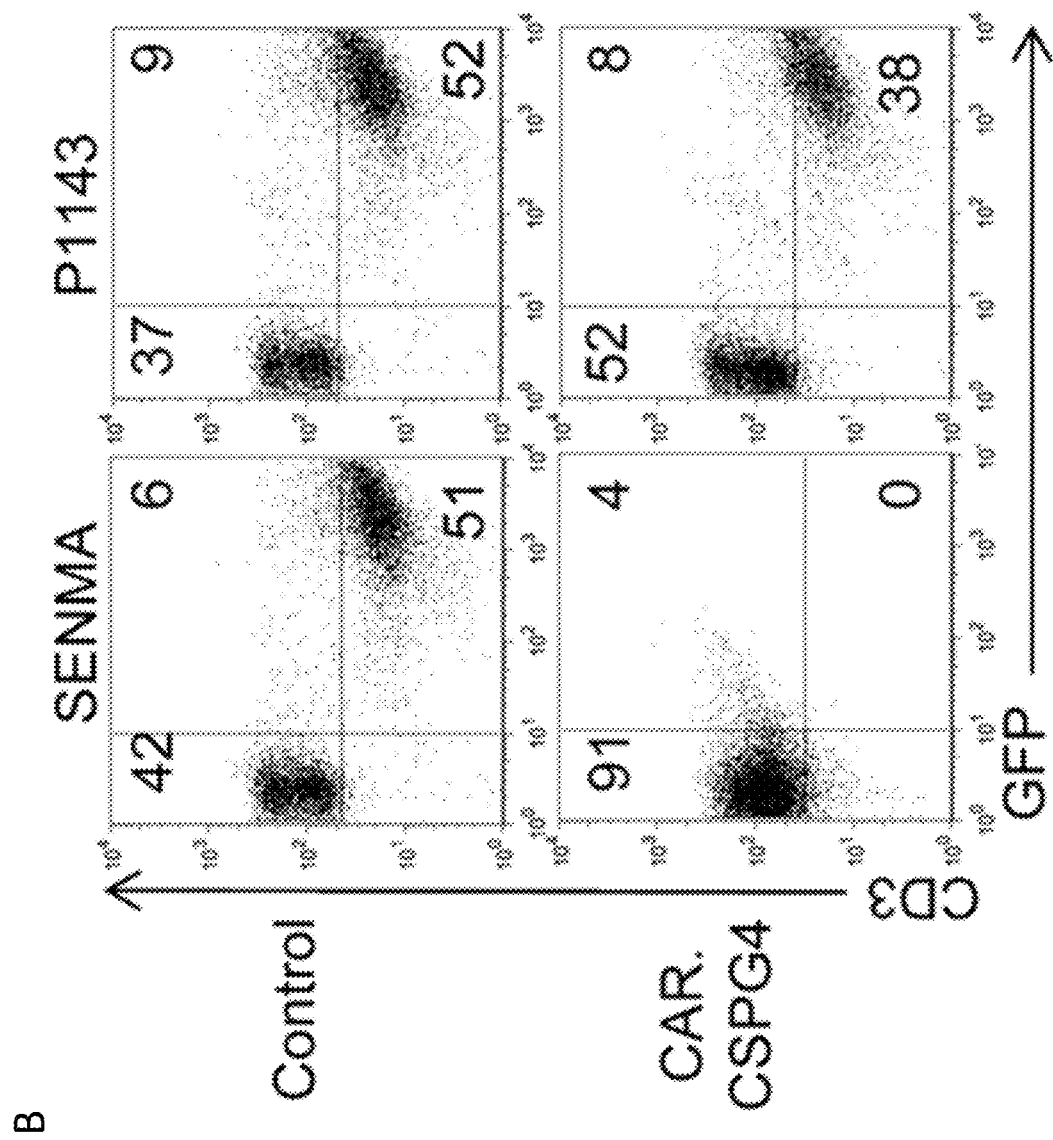
Figure 3:
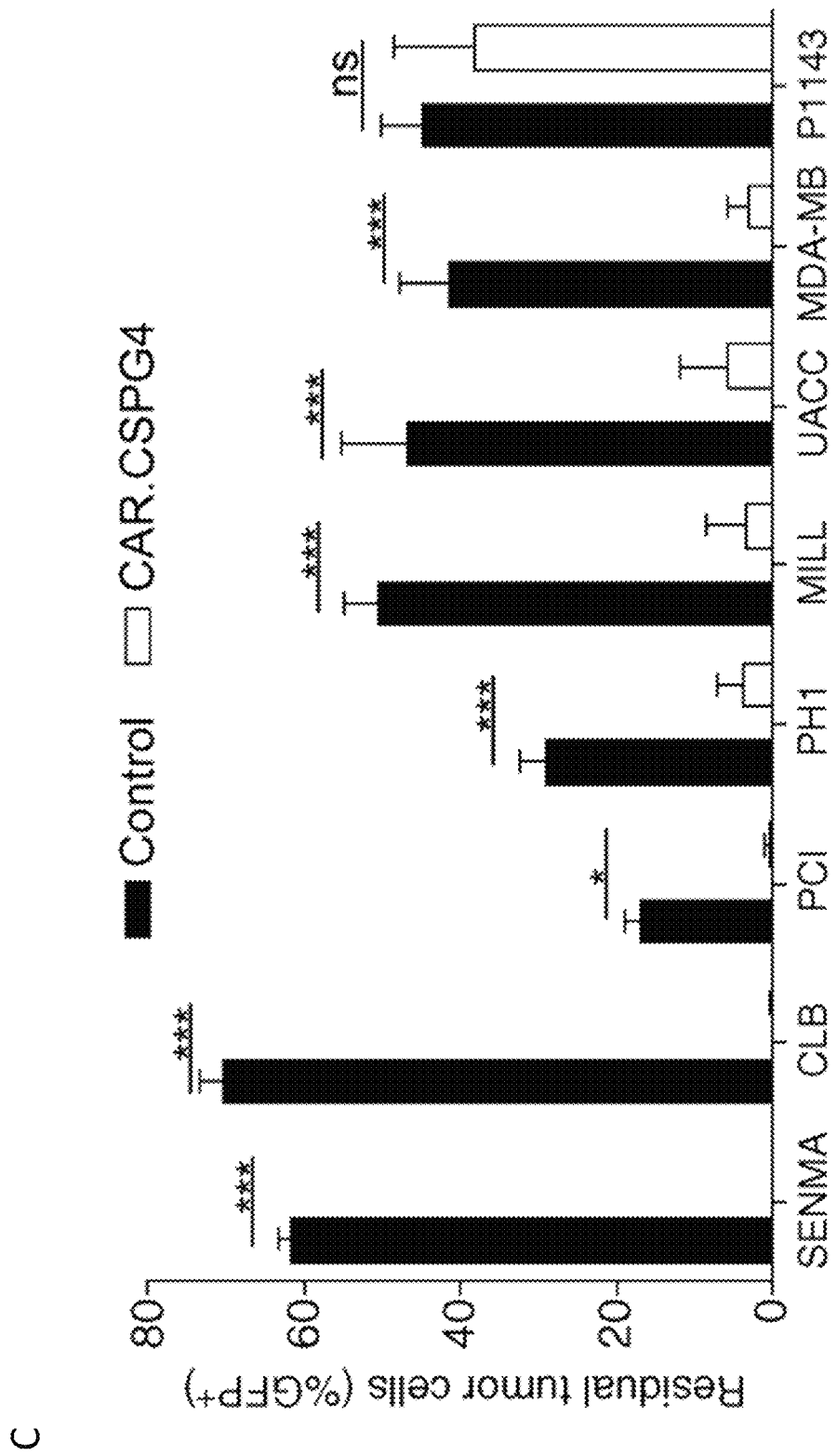
Figure 3:
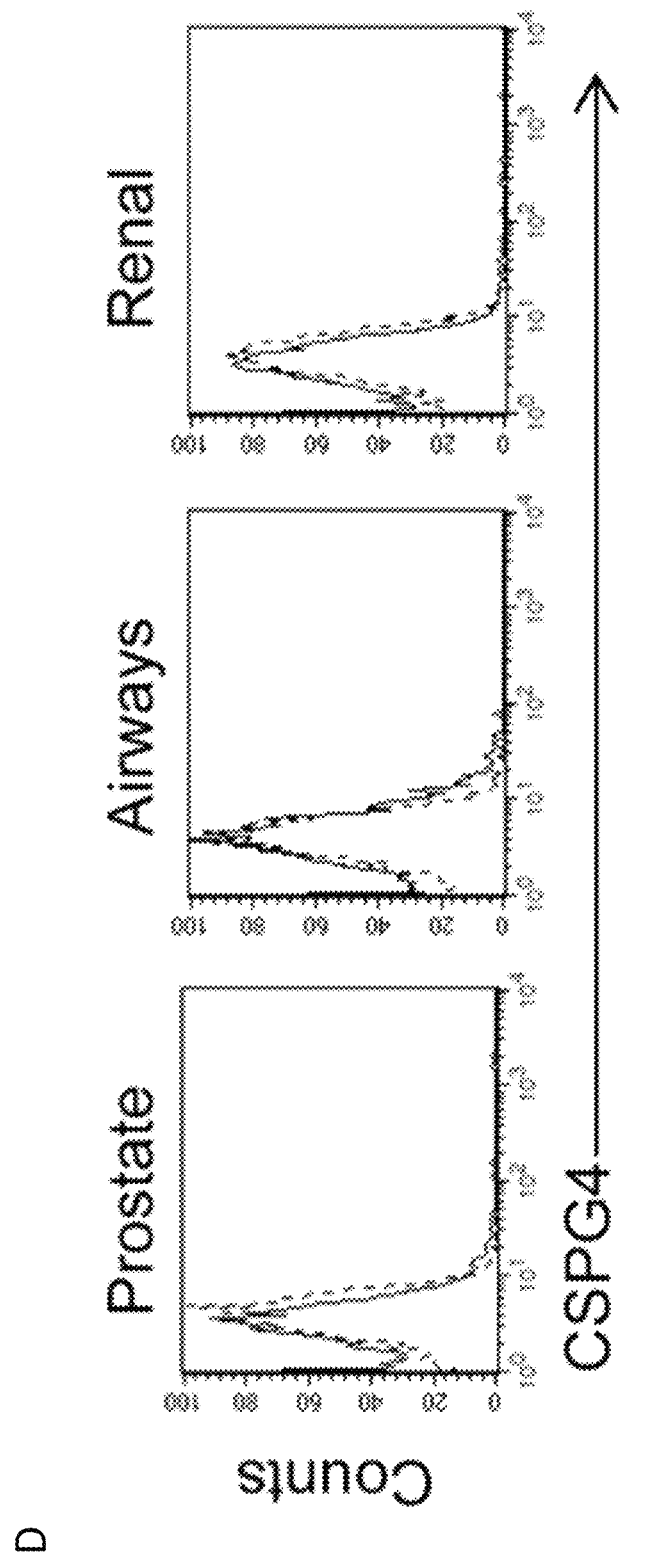
Figure 3:
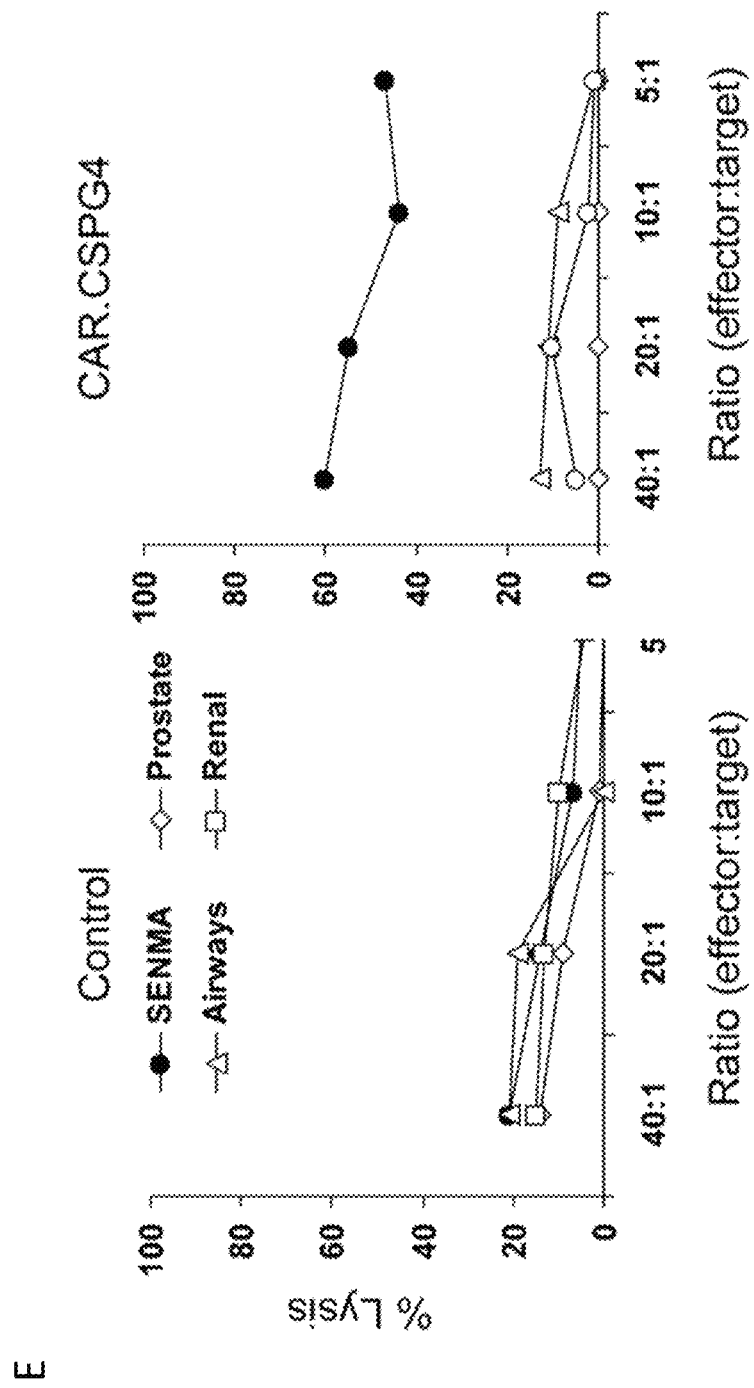

FIG. 3. Cytotoxic function of CAR.CSPG4+ T cells against CSPG4+ tumors but not against epithelial cells from lung, kidney and prostate. Panel A. Cytotoxic activity of control T cells and CAR.CSPG4$^+$ T cells evaluated in a 6 hour $^{51}$Cr release assay. Target cells used were the CSPG4$^+$ tumor cell line (SENMA), CSPG4– target cell line (P1143) and K562 to quantify natural killer activity. Data show averages and SD results of T cells from 4 donors. Panel B. Co-culture experiments of control and CAR.CSPG4$^+$ T cells with GFP+ tumor cell lines, assessed by flow cytometry 72 hours later. The plots describe a representative experiment of T cells co-cultured with SENMA (CSPG4$^+$ target) or P1143 (CSPG4$^-$ target). Numbers represent percentages of cells per quadrant. Panel C. Summary of co-culture experiments of control and CAR.CSPG4$^+$ T cells against a panel of CSPG4$^+$ tumor targets. Data represent averages±SD of 4 donors. *=p<0.05, and ***=p<0.001. Panel D. FACS analysis of CSPG4 expression in primary epithelial cells derived from normal small airway, kidney and prostate. Dotted and bold lines indicate isotype and CSPG4 mAbs, respectively Panel E. Cytotoxic activity of control T cells and CAR.CSPG4$^+$ T cells from a representative donor of two independent experiments evaluated in a 5 hour $^{51}$Cr release assay against these normal epithelial cells.

Figure 4:
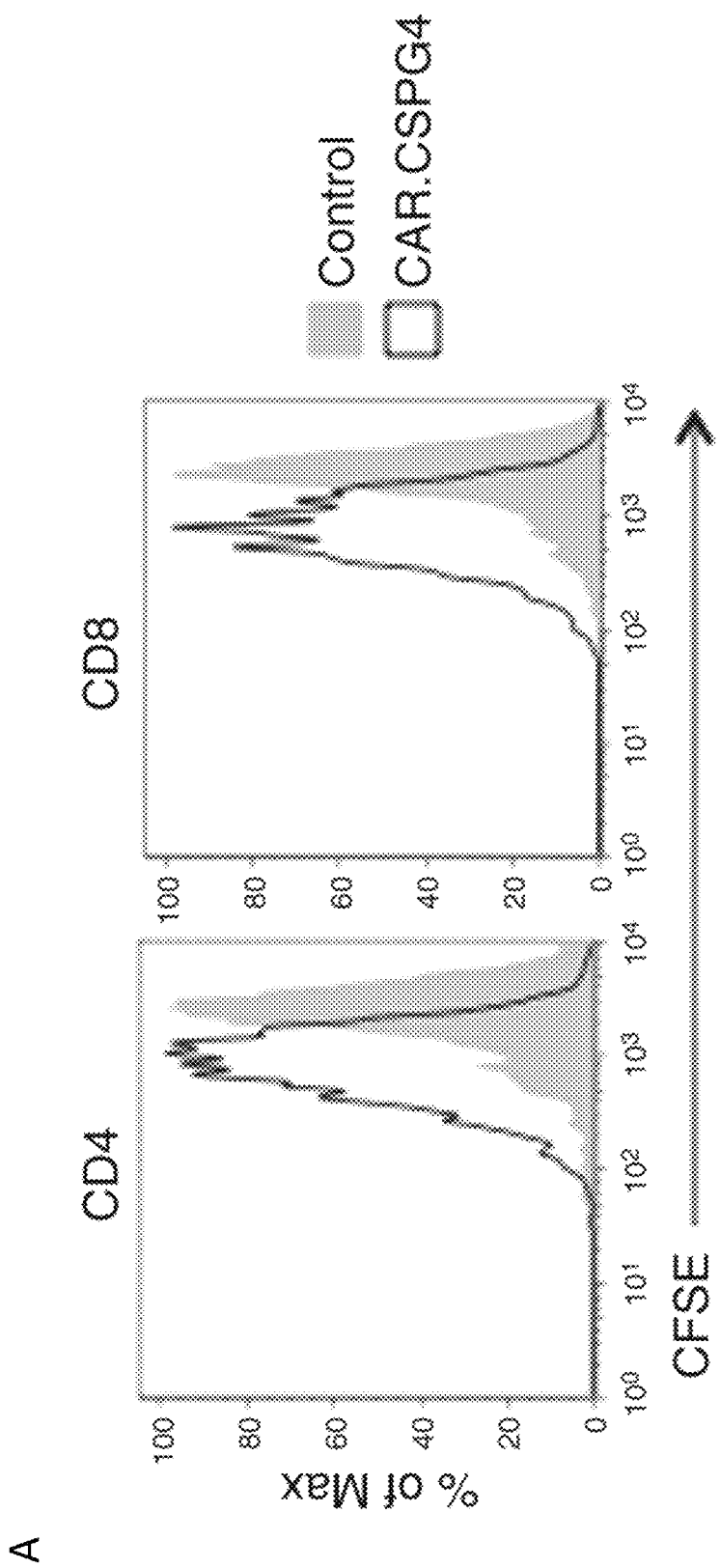
Figure 4:
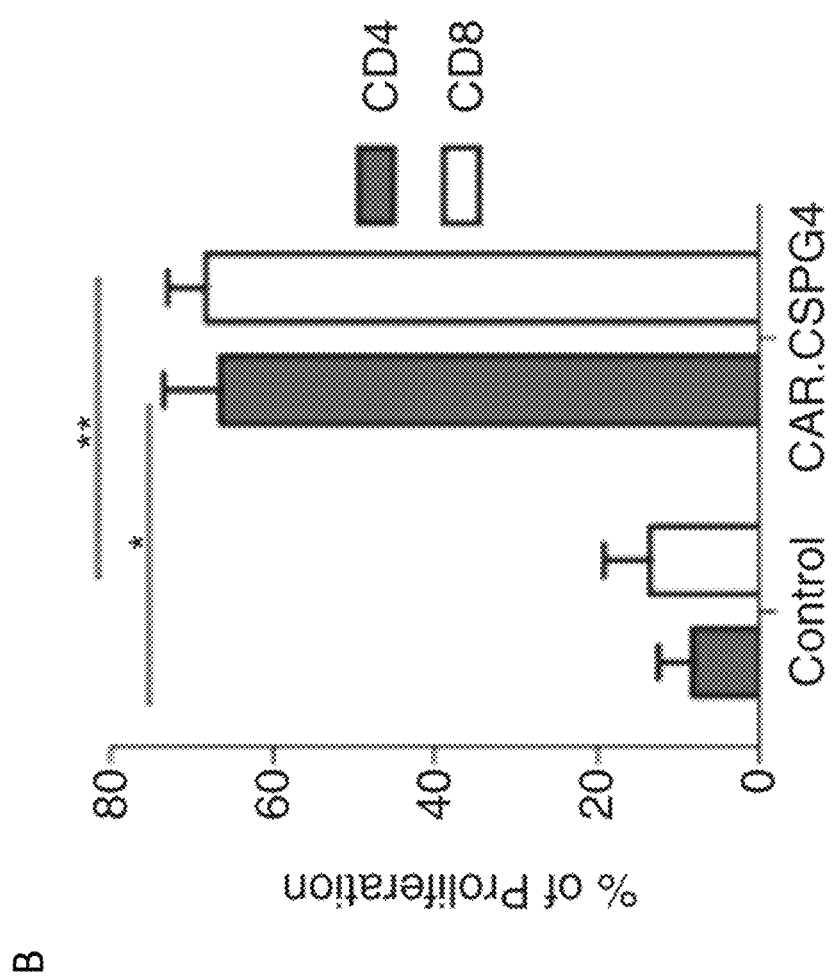
Figure 4:
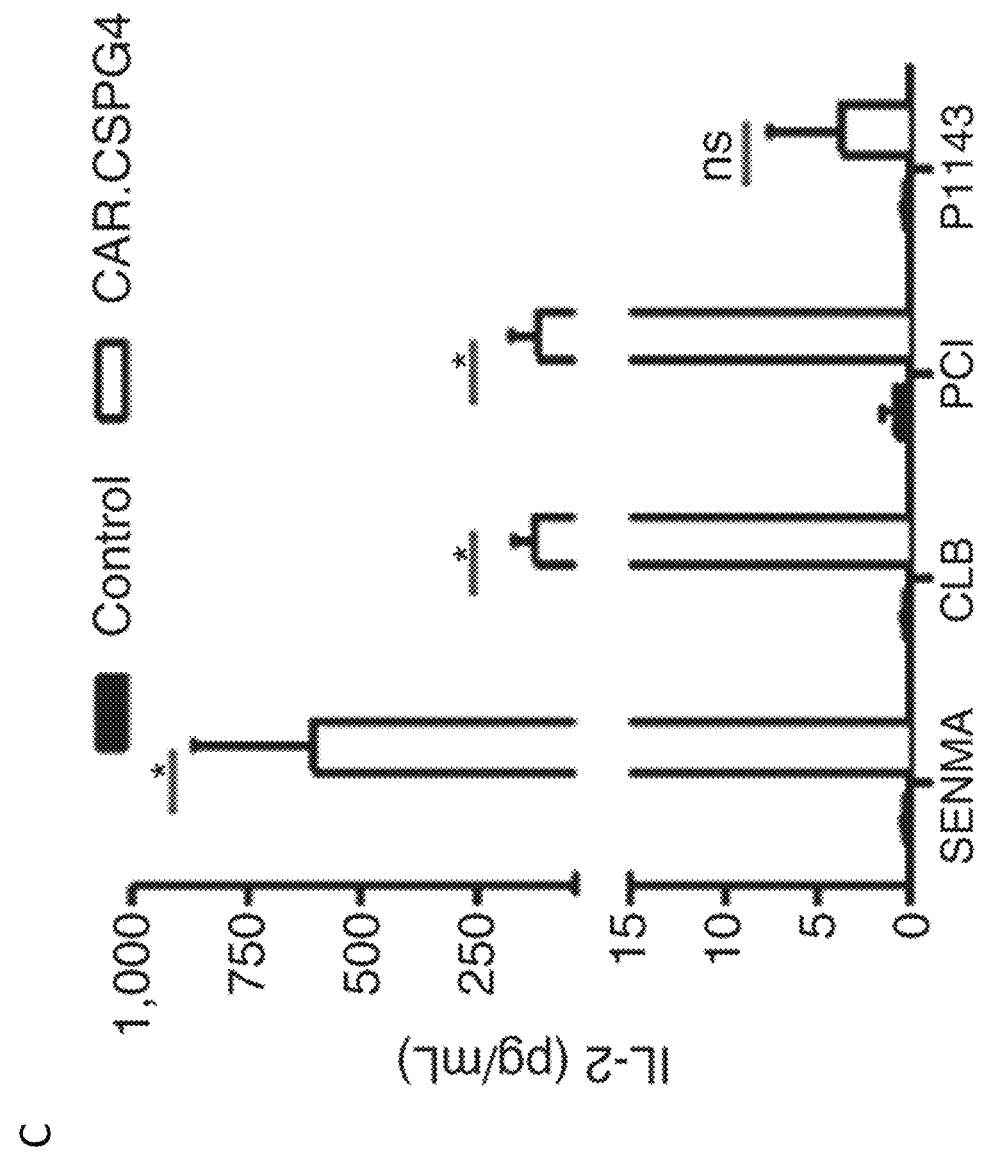
Figure 4:
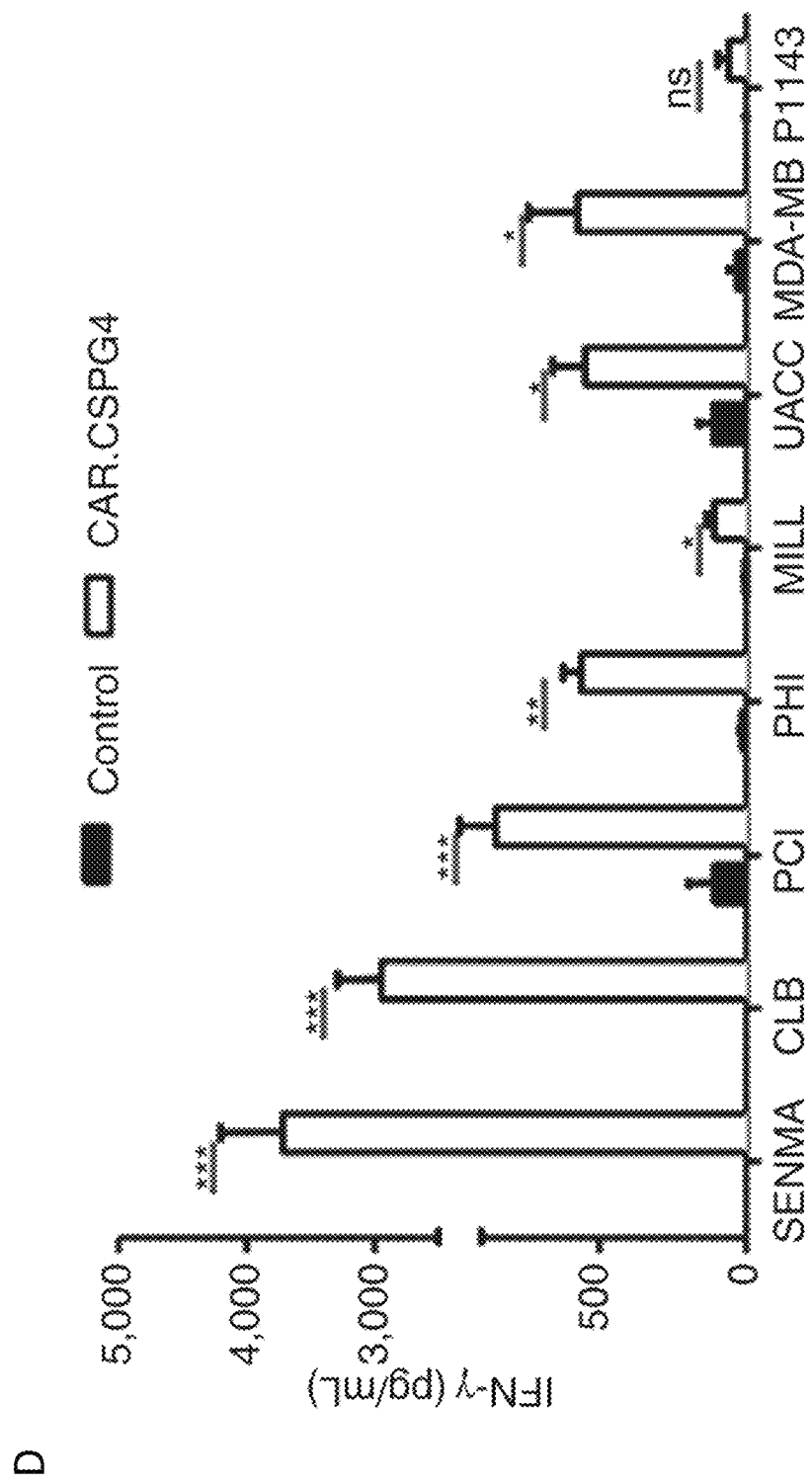

FIG. 4. T lymphocytes transduced with CAR.CSPG4 proliferate and release IL-2 and IFNγ upon specific antigen engagement. Panel A. Control and CAR.CSPG4$^+$ T cells, labeled with CFSE, were stimulated with irradiated CSPG4$^+$ (SENMA) tumor target. The panel illustrates the CFSE dilution in CD4 or CD8 gated T cells after 96 hours of culture for a representative donor. Panel B. Summary of 3 independent CFSE dilution assays. Data represents mean±SD. Panel C. IL-2 cytokine-release assessment using specific ELISA by T lymphocytes transduced with CAR.CSPG4 and control T cells 24 hours post co-culture (E:T ratio 5:1) with either CSPG4$^+$ tumors or CSPG4$^-$ target cells (P1143). Results of 5 experiments are presented with mean±SD. Panel D illustrates the detection of IFNγ in the same culture supernatant. Results of 5 experiments with mean±SD are shown. *=P<0.05, =p<0.01, and *=p<0.001.

Figure 5:
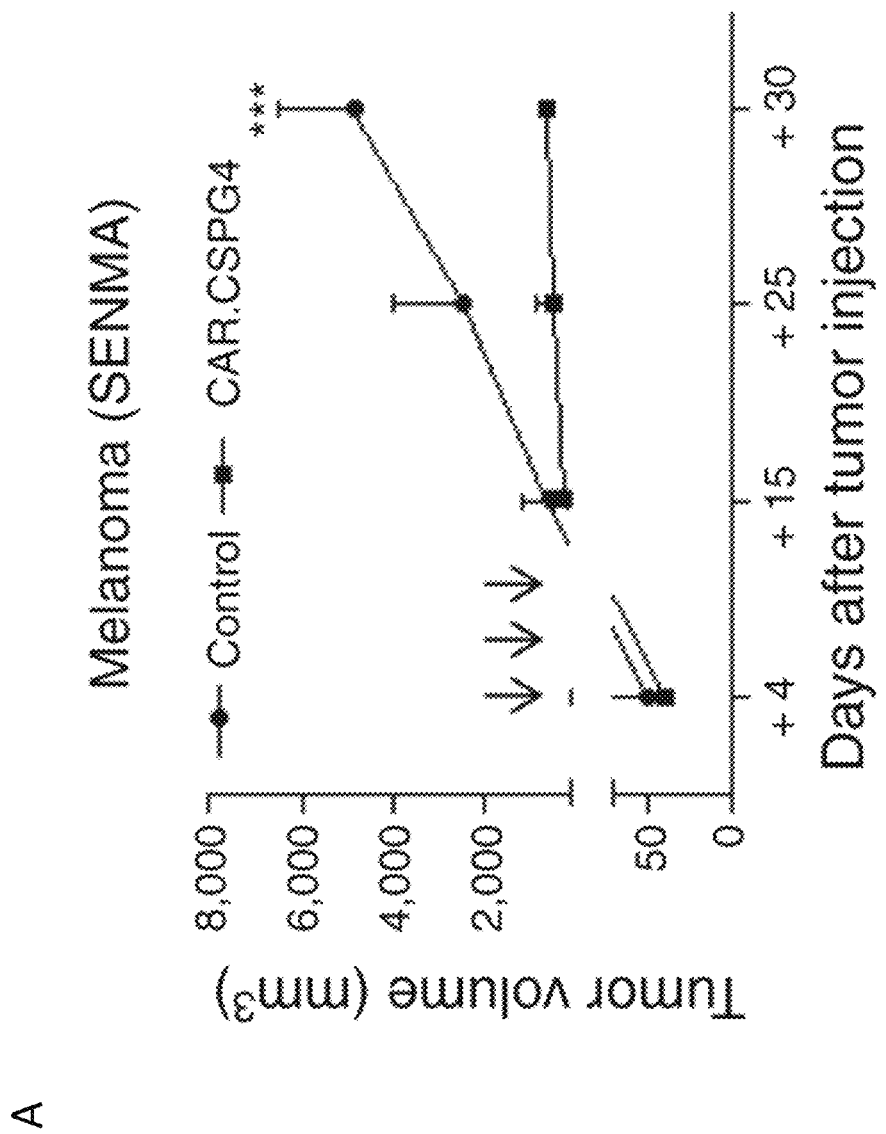
Figure 5:
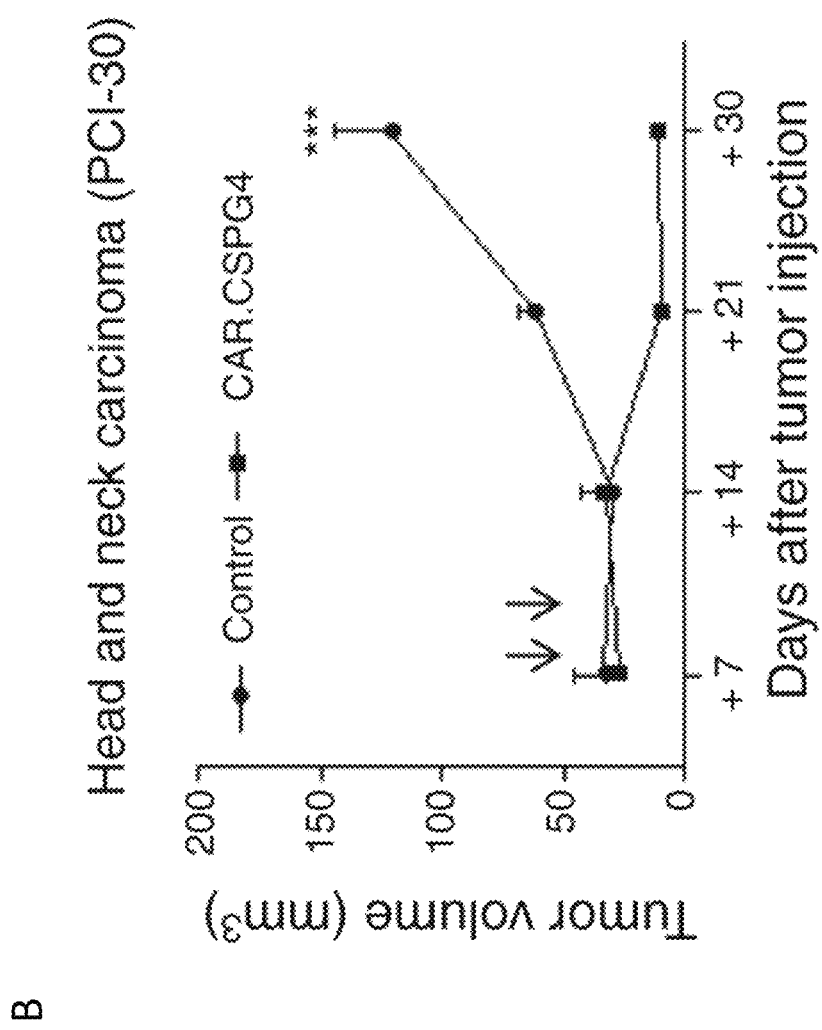
Figure 5:
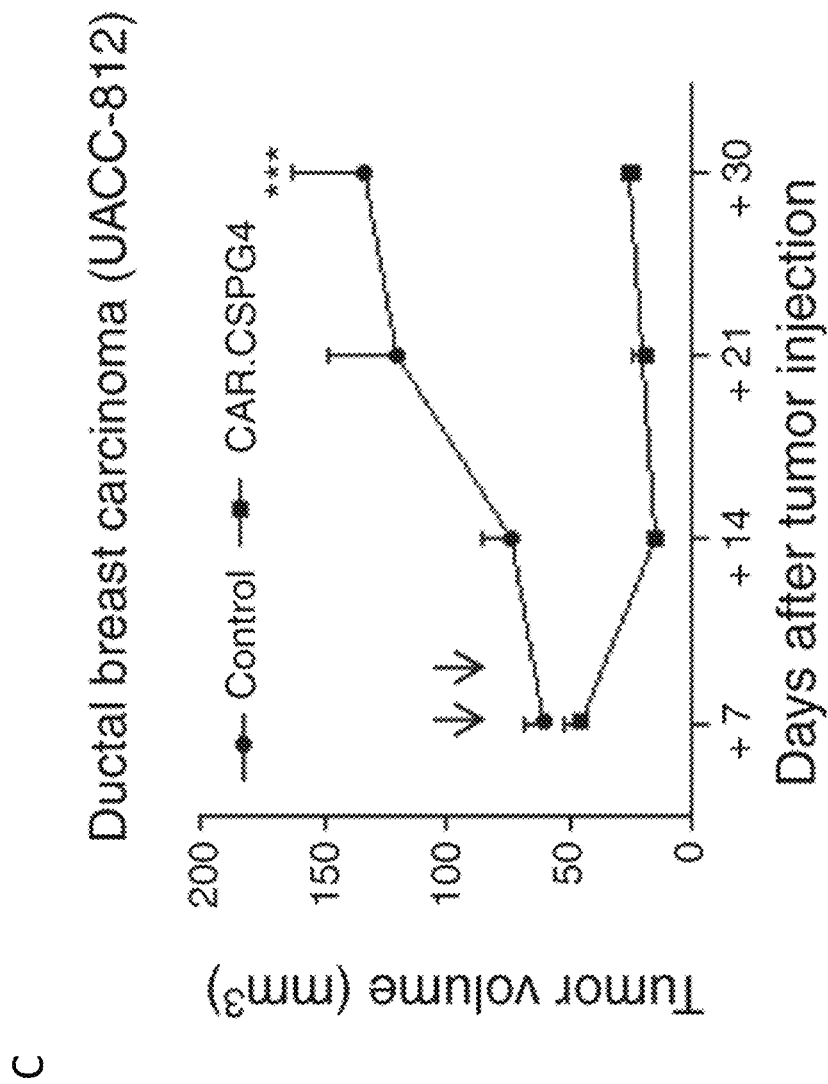

FIG. 5. CAR.CSPG4+ T lymphocytes control tumor growth in vivo. Panels show tumor growth, assessed by caliper measurement, of NSG mice engrafted subcutaneously with melanoma (SENMA) (Panel A), HNSCC (PCI-30), (Panel B) or breast carcinoma (UACC-812) (Panel C) cell lines and infused i.v. with either CAR.CSPG4$^+$ (closed squares) or control (closed circles) T lymphocytes. Arrows indicate T-cell infusions. Shown are mean±SD from 15 mice per group (3 independent experiments) for the melanoma model and 10 mice per group (2 independent experiments) for the HNSCC model and breast carcinoma models. ***=p<0.001.

Figure 6:
Figure 6:
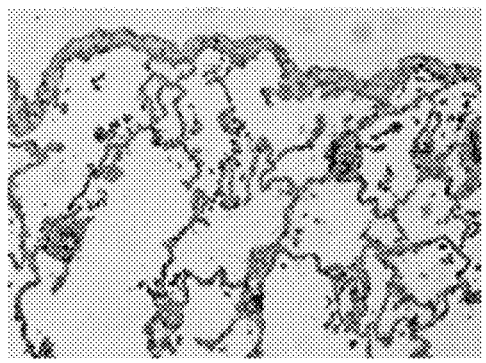
Figure 6:
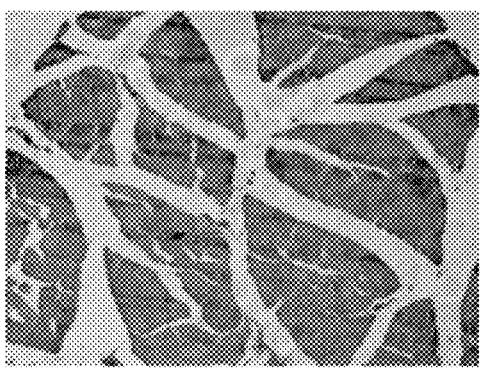
Figure 6:
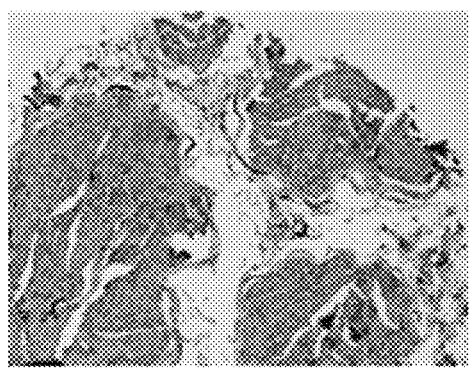
Figure 6:
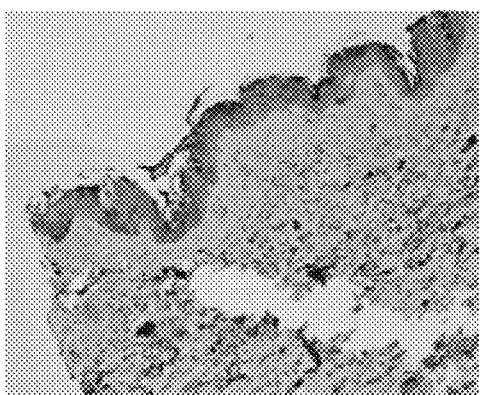
Figure 6:
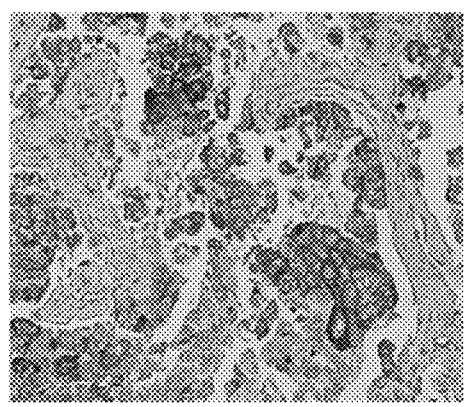

FIG. 6. Immunohistochemistry of normal tissue arrays. Representative immunohistochemistry of normal tissue arrays. Endometrium, lung, skeletal muscle, nerve, skin, and a lung carcinoma are shown. 200× magnification.

Figure 7:
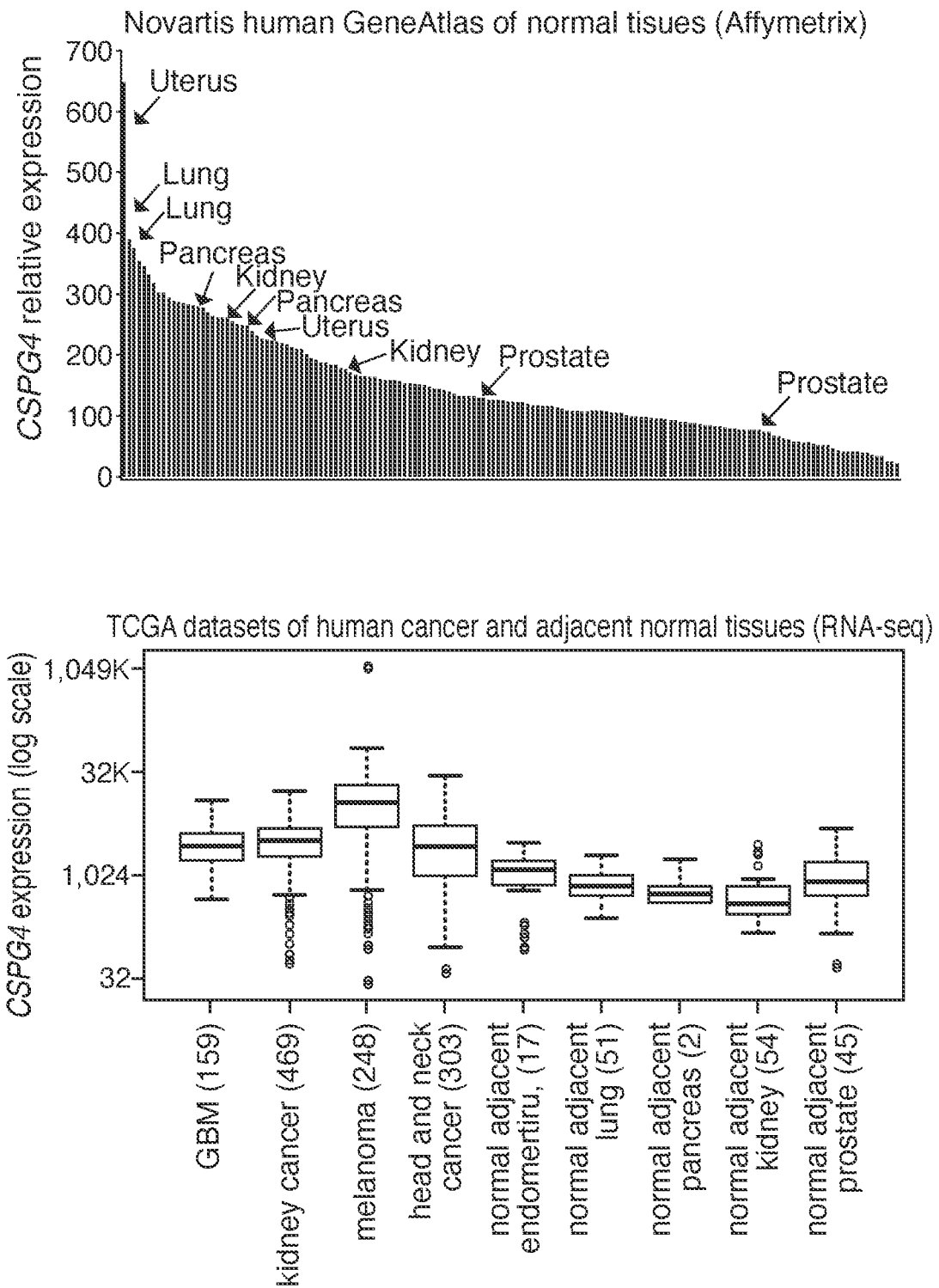

FIG. 7. CSPG4 mRNA expression levels in normal tissues. Top panel, CSPG4 expression across normal human tissues represented in the Novartis GeneAtlas dataset (http://biogps.org). Values represented are relative and the average of Affymetrix probe sets 214297_at and 204736_s_at. Highlighted are normal tissues for which corresponding normal adjacent tissue data were available in TCGA datasets. Bottom panel, CSPG4 mRNA expression by TCGA in a variety of solid tumors (featured in main FIG. 1D) and normal adjacent tissues (the normal tissues being also represented in GeneAtlas), with the cancers showing higher CSPG4 levels over that of the normal samples. Note shown is log 2 scale.

Figure 8:
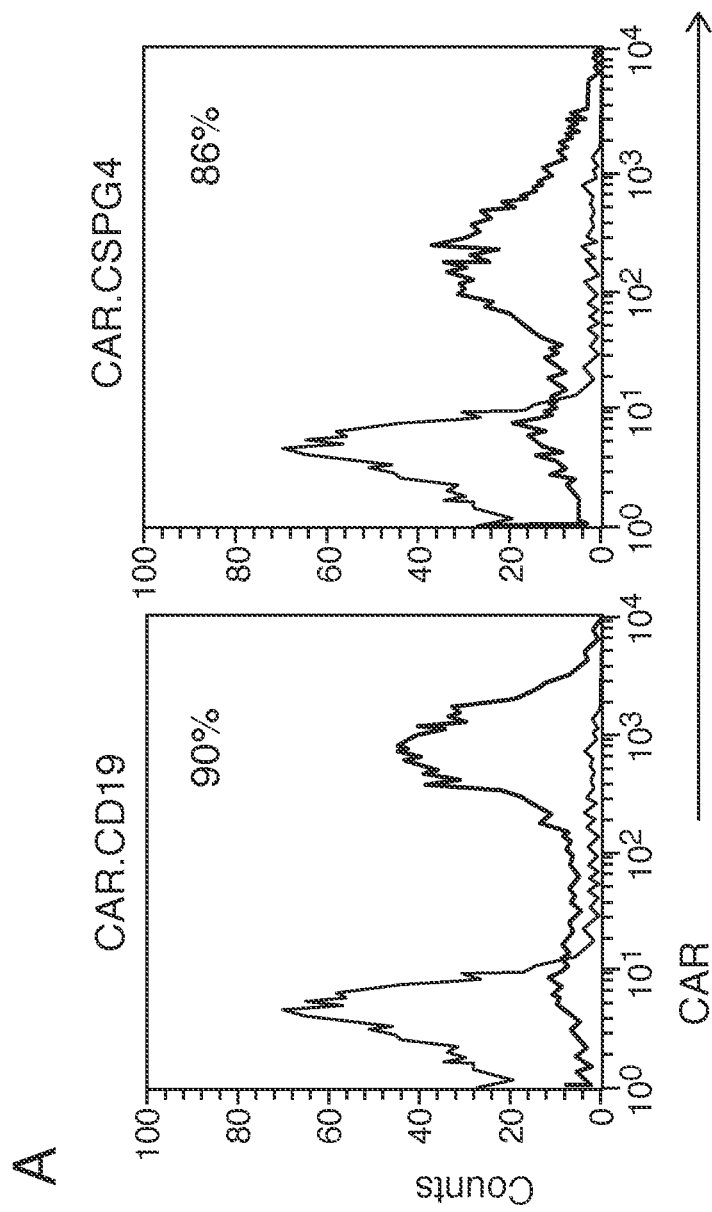
Figure 8:
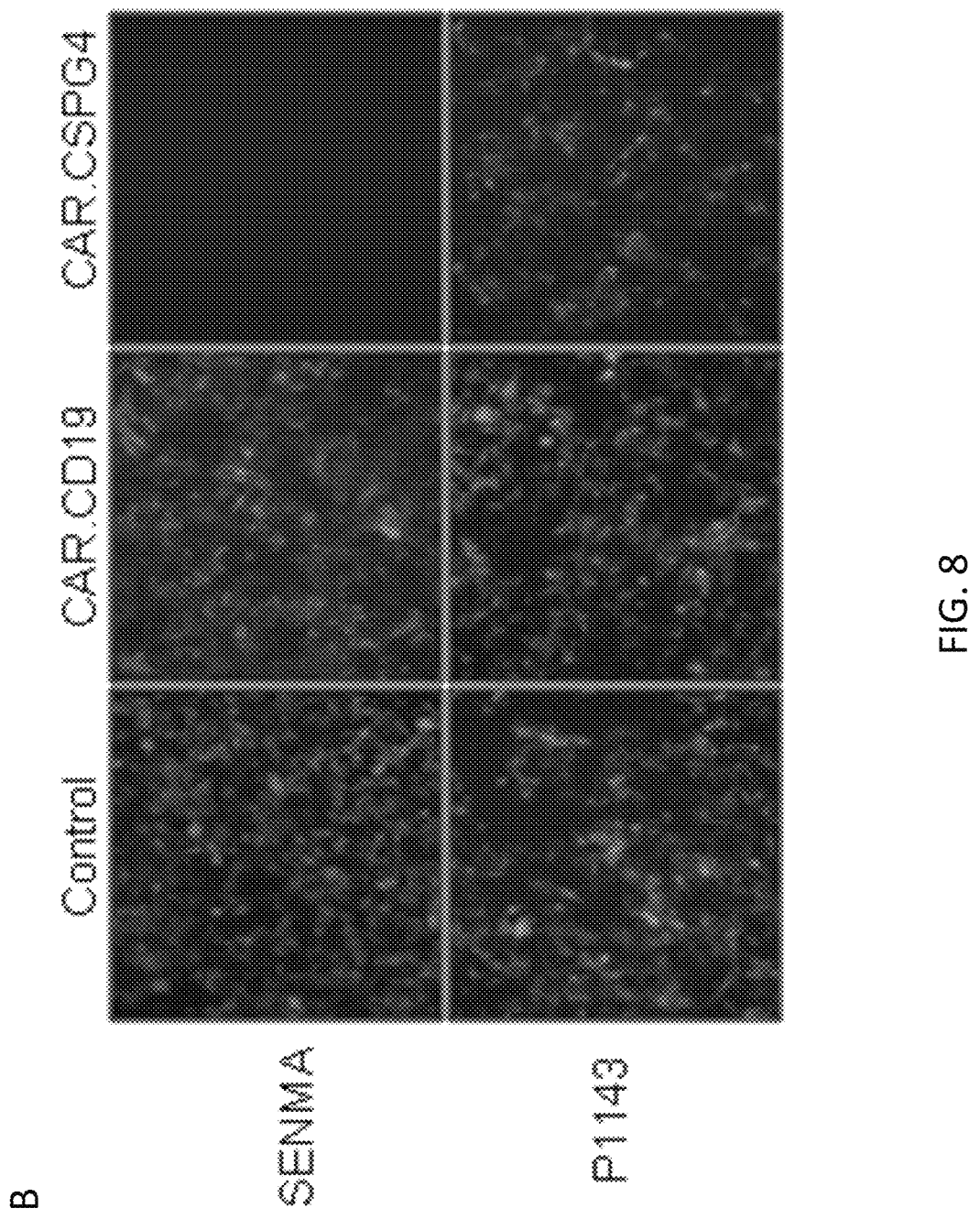
Figure 8:
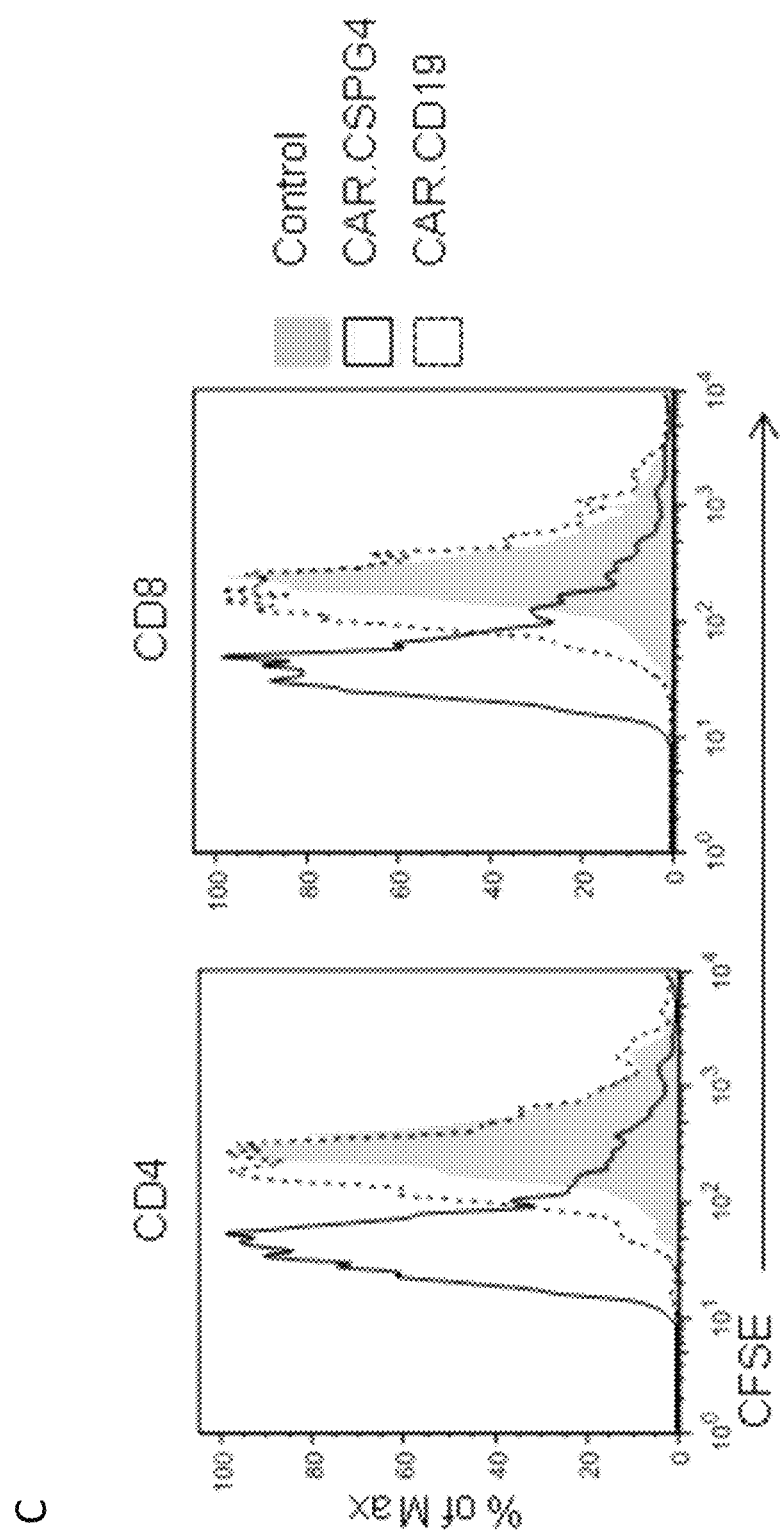
Figure 8:
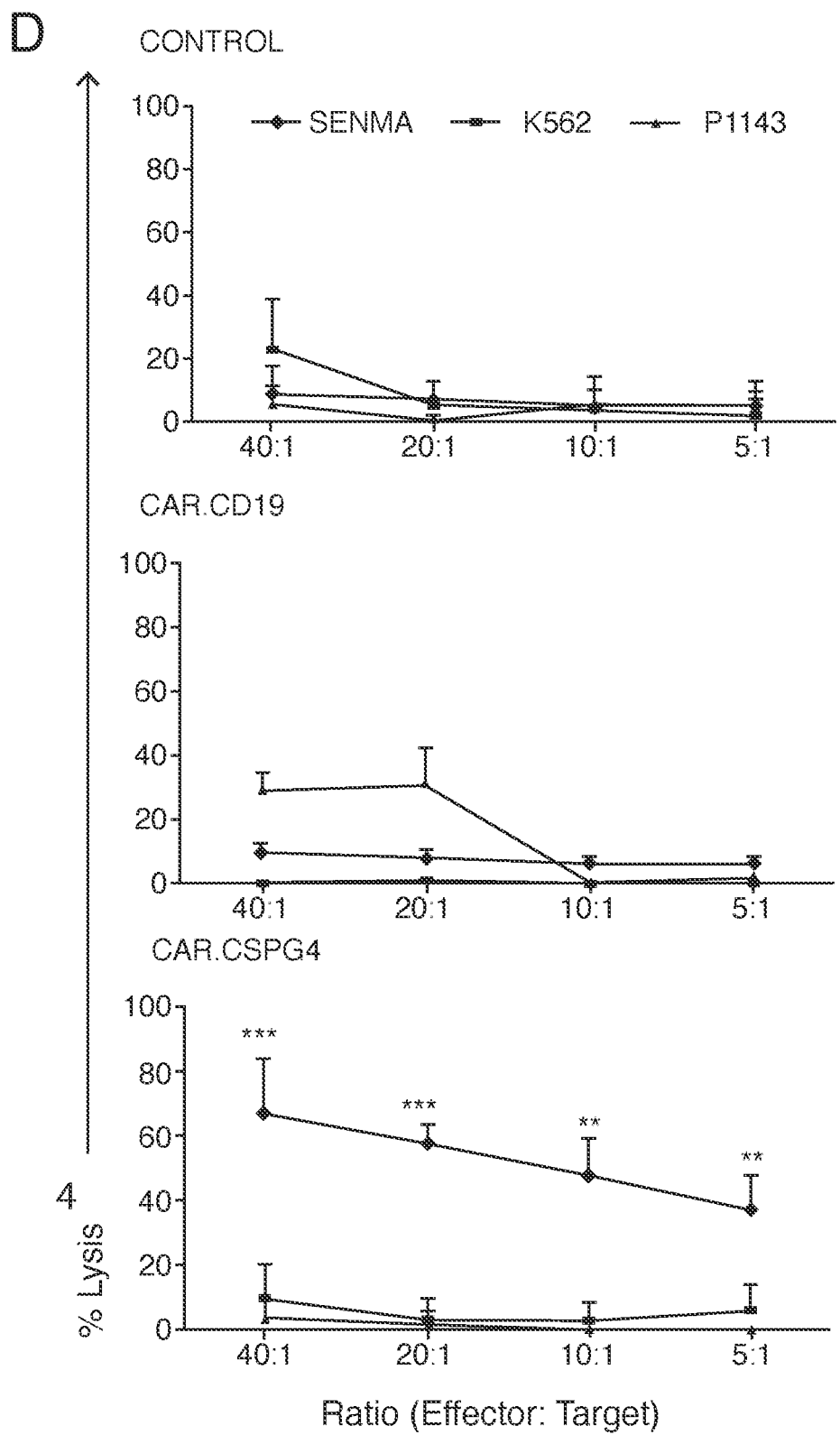

FIG. 8. Comparison of CAR.CSPG4+ and CAR.CD19+ T lymphocytes. Panel A. Expression of CAR.CD19 and CAR.CSPG4 in T lymphocytes after retroviral transduction, as assessed by FACS. Panel B. Co-culture experiments in which CAR.CSPG4+ T cells, CAR.CD19+ T cells, and control (non-transduced) cells were cultured with GFP+ tumor cell lines. Pictures illustrate the elimination of CSPG4+eGFP+ target (SENMA) by CAR.CSPG4+ T cells and not by CAR.CD19$^+$ T cells or control T cells after 72 hours of co-culture. The CSPG4=cell lines P1143 was not targeted by either CAR.CSPG4+ T cells or CAR.CD19$^+$ T cells. Panel C. Proliferation of control (non-transduced), CAR.CD19$^+$, and CAR.CSPG4$^+$ T cells upon stimulation with CSPG4+ target in a 96 hour CFSE dilution assay. Data are representative of three independent experiments using irradiated SENMA tumor cells. Panel D. Control (non-transduced), CAR.CD19$^+$, and CAR.CSPG4$^+$ T cells were evaluated in a 6 hour cytotoxicity assay against SENMA (CSPG4$^+$), K562 (natural killer cell target), and P1143 (CSPG4$^-$). Data represents the average of three experiments with mean±SD.

Figure 9:
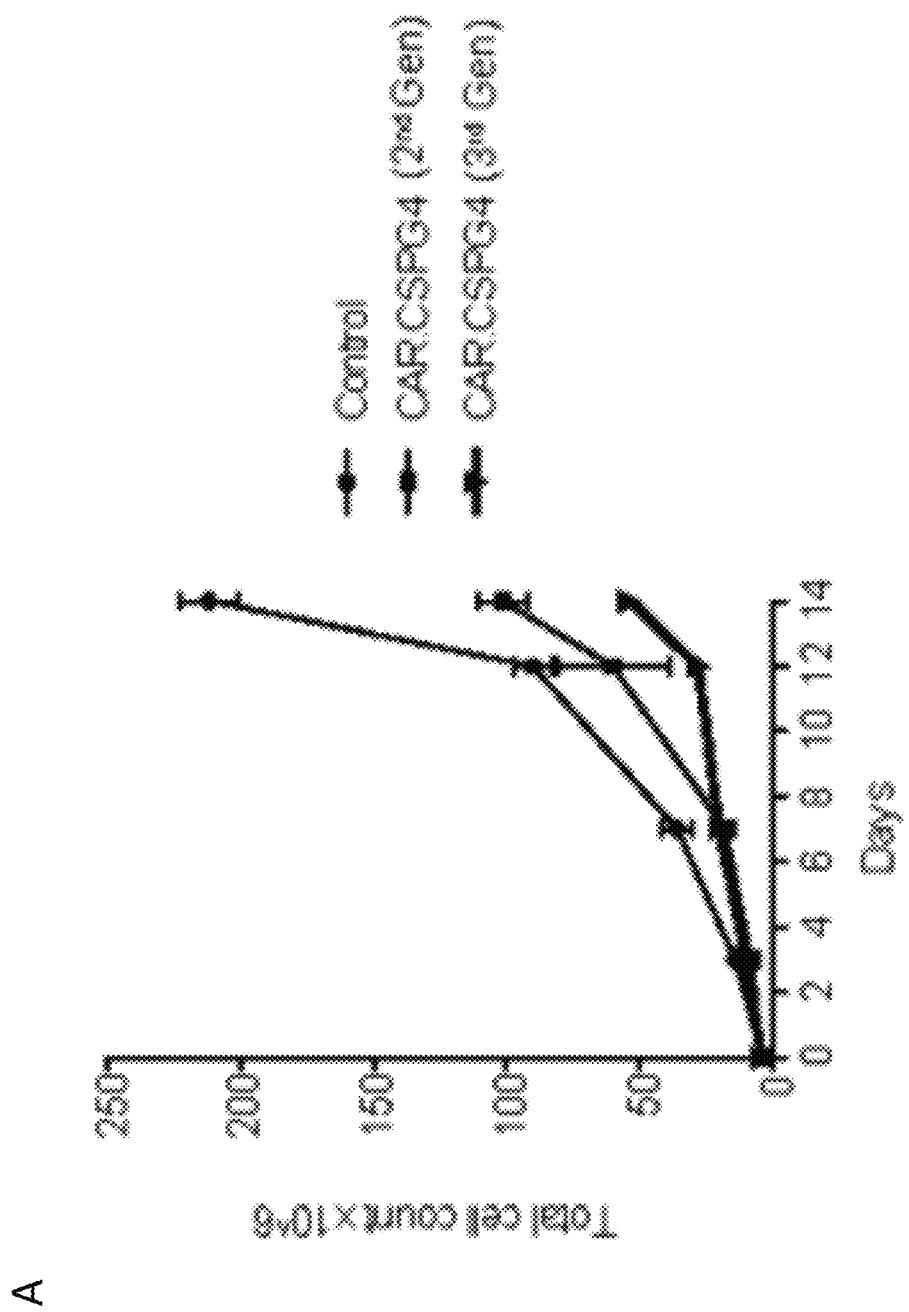
Figure 9:
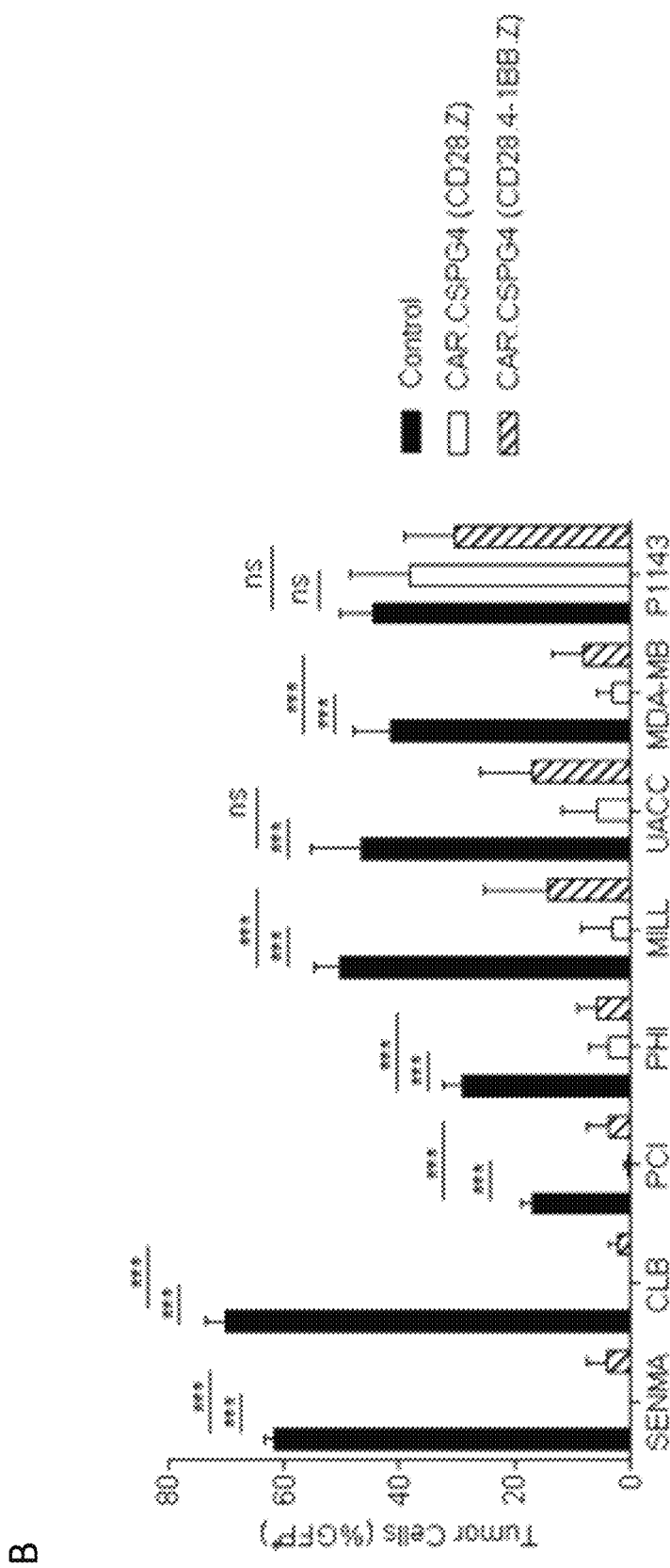

FIG. 9. Expansion and antitumor activity of T cells expressing a second versus a third generation CAR.CSPG4. Panel A illustrates the expansion of control, CAR.CSPG4 (2nd gen, CD28 costimulation), and CAR.CSPG4 (3rd gen, CD28/4-1BB costimulation) within 14 days of culture. Data represents the average of 4 T-cell lines with mean±SD. Panel B. Summary of co-culture experiments of anti-tumor activity of control, CAR.CSPG4$^+$ T cells either 2nd or 3rd generation against a panel of CSPG4$^+$ tumor targets. Data represent averages of 3 donors with mean±SD. *=p<0.05, and ***=p<0.001.

Figure 10:
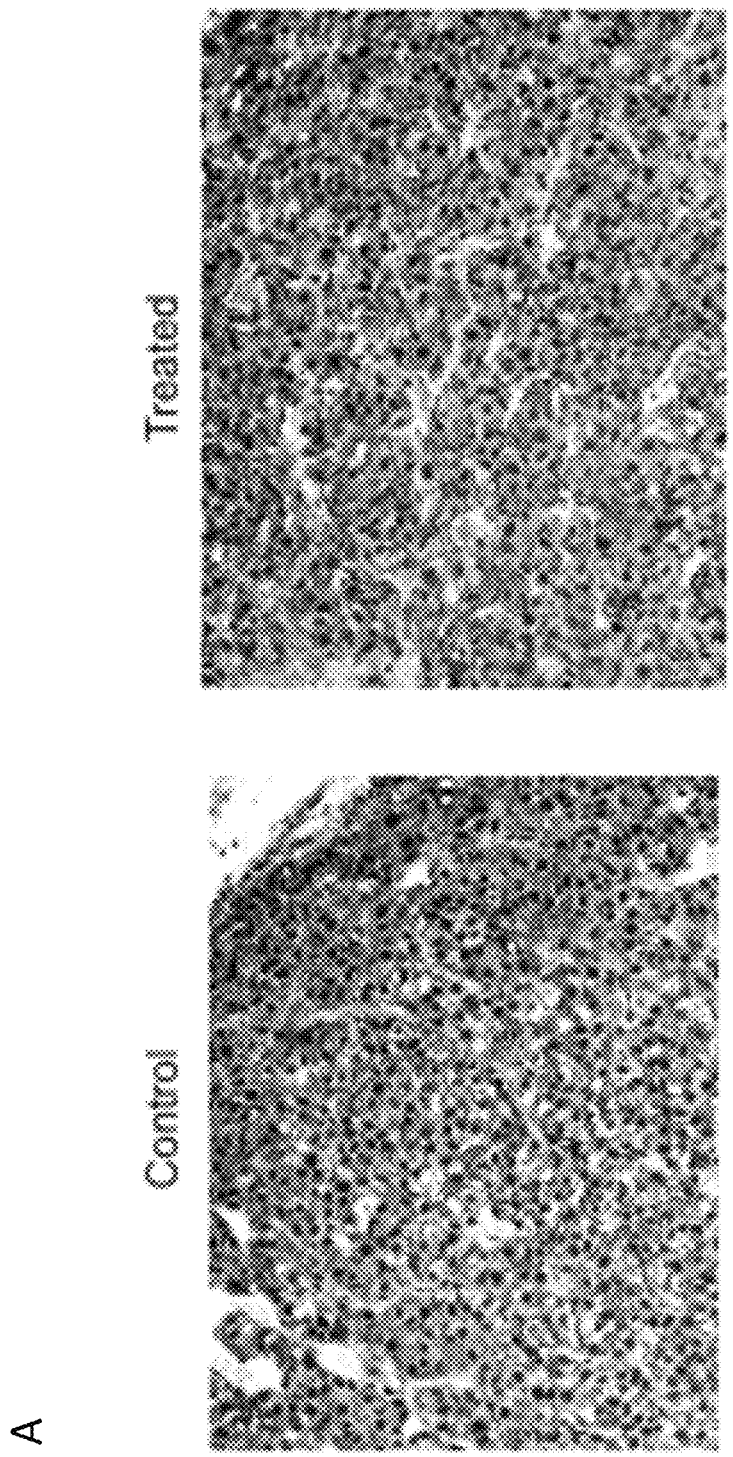
Figure 10:
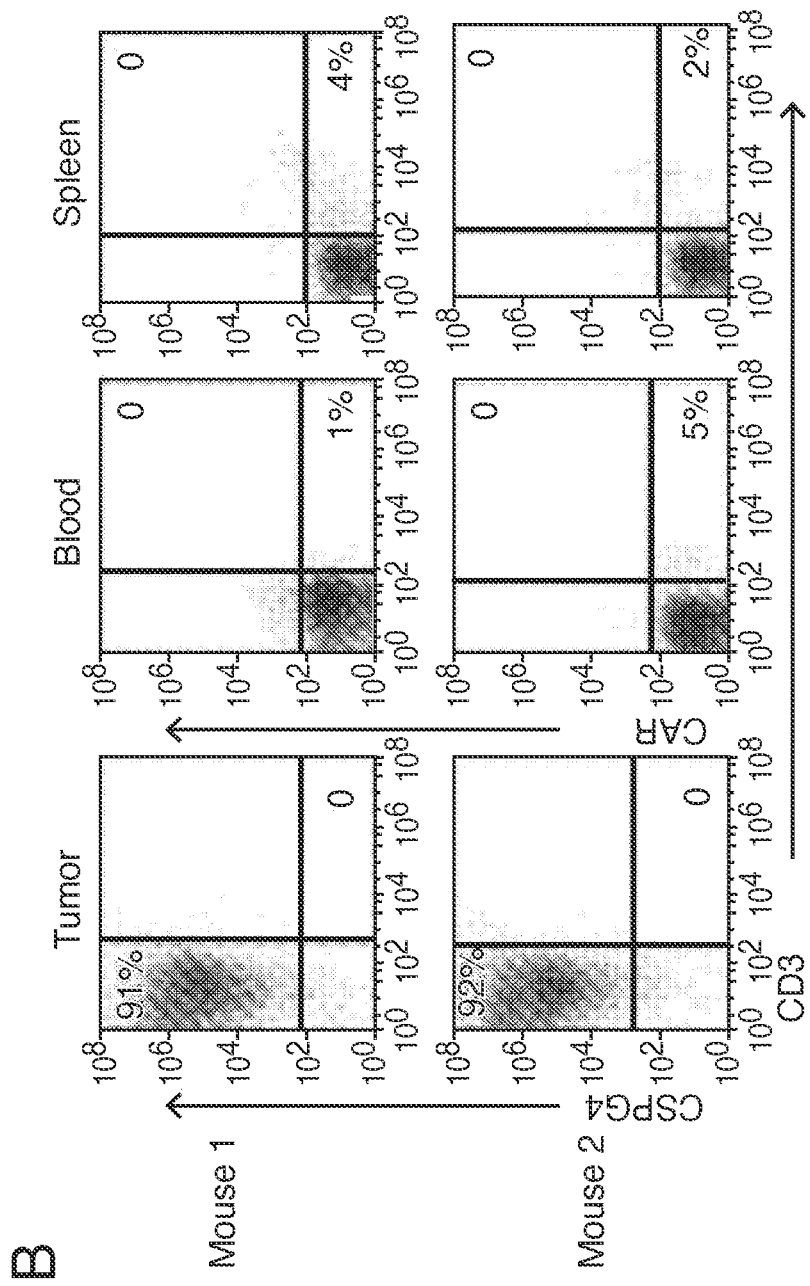
Figure 10:
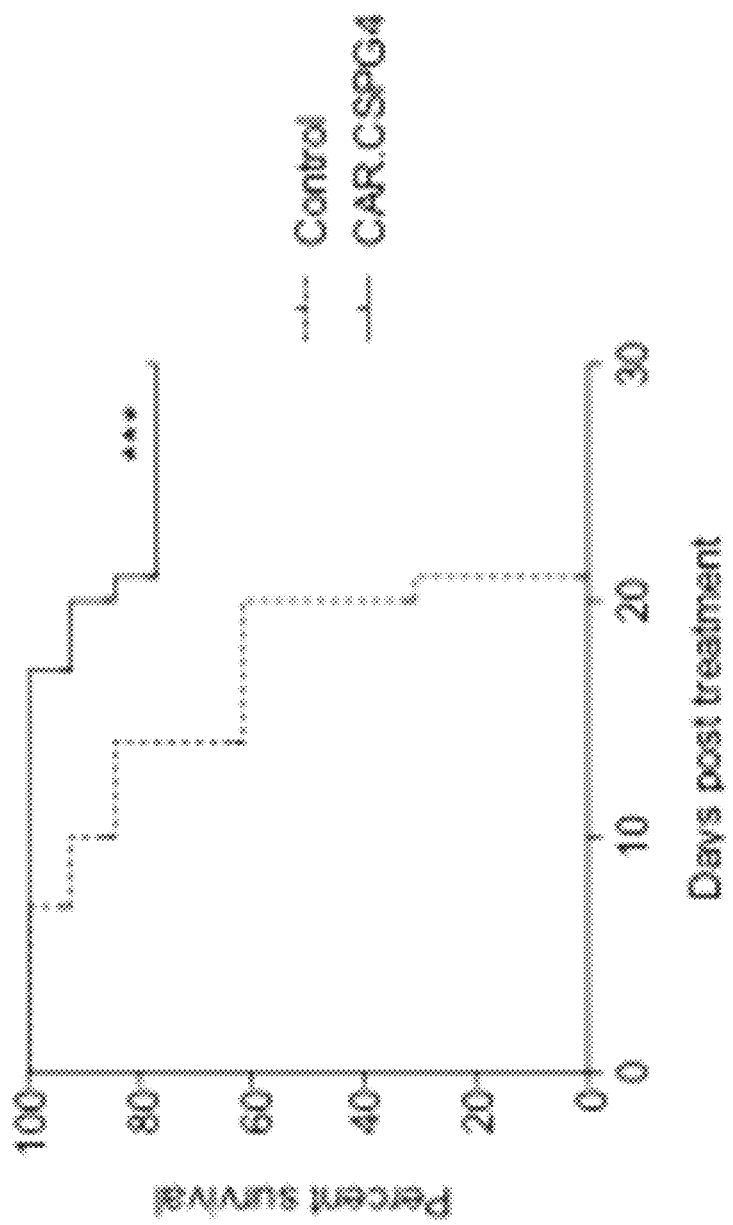

FIG. 10. Immunohistochemistry, flow cytometry and survival curve analysis of the melanoma xenograft model. Panel A illustrates the expression of CSPG4 in tumor samples (SENMA) isolated 30 days after infusion of either CAR.CSPG4$^+$ T cells or control T cells. Panel B. FACs analysis to detect tumor cells and CD3+ T cells in tumor biopsy, blood and spleen collected from mice at day 30 post tumor (SENMA) injection. Panel C. Survival curve of the melanoma xenograft model. Data are representative of 15 control and treated mice. Log-rank test: p<0.0001.

DETAILED DESCRIPTION

As used herein the specification, "a" or "an" may mean one or more. As used herein in the claim(s), when used in conjunction with the word "comprising", the words "a" or "an" may mean one or more than one. As used herein "another" may mean at least a second or more. In specific embodiments, aspects of the subject matter may "consist essentially of" or "consist of" one or more elements or steps of the subject matter, for example. Some embodiments of the subject matter may consist of or consist essentially of one or more elements, method steps, and/or methods of the subject matter. It is contemplated that any method or composition described herein can be implemented with respect to any other method or composition described herein.

I. General Embodiments

Adoptive transfer of CAR-redirected T lymphocytes represents a useful therapy for patients with malignancies. Here the applicability of this strategy is extended to a broad array of solid tumors by targeting the CSPG4 antigen; this antigen is over-expressed by numerous tumor types while having negligible expression in normal tissues. The disclosure provides evidence that CSPG4-redirected T cells can control the growth of at least human melanoma, HNSCC and breast cancer both ex vivo and in vivo in xenograft models.

Particular aspects of the disclosure include methods of treating CSPG4-expressing cancers. The cancers may be head and neck cancer, mesothelioma, breast cancer, glioblastoma, or renal cancer, for example, and in at least some cases the cancer is not melanoma. In specific embodiments of the disclosure, a particular scFv for CSPG4 is employed, and in particular cases the CSPG4 scFv is not derived from the murine mAb 225.28S. In at least one specific case, the methods are for treating CSPG4-expressing cancer that is not melanoma and wherein the CSPG4 CAR does not employ a scFv derived from the murine mAb 225.28S. In at least a specific case, the methods are for treating CSPG4-expressing cancer that is not melanoma and wherein the CSPG4 CAR employ scFv 763.74.

Indicia of successful treatment could be, e.g., detectable reduction in the growth of a tumor (e.g., as seen by MRI or the like), or reduction in one or more symptoms of a cancer that expresses CSPG4, for example.

II. Chondroitin Sulfate Proteoglycan 4

Embodiments of the disclosure use methods and/or compositions that include targeting of Chondroitin Sulfate Proteoglycan 4 (CSPG4) on a cancer cell.

A skilled artisan recognizes that Chondroitin Sulfate Proteoglycan 4 has multiple names, including at least Melanoma-Associated Chondroitin Sulfate Proteoglycan; Chondroitin Sulfate Proteoglycan 4 (Melanoma-Associated); Chondroitin Sulfate Proteoglycan NG2; Melanoma Chondroitin Sulfate Proteoglycan; MCSP; MCSPG; MSK16; NG2; High molecular weight-melanoma associated antigen (HMW-MAA); MEL-CSPG; EC 2.7.8; and EC 3.6.3. An example of a CSPG4 nucleic acid sequence is provided under the National Center for Biotechnology Institute's GenBank® accession number NM 001897, which is incorporated by reference herein in its entirety. An example of a CSPG4 amino acid sequence is provided under the National Center for Biotechnology Institute's GenBank® accession number NP_001888, which is incorporated by reference herein in its entirety.

III. Chimeric Antigen Receptors

Genetic engineering of human T lymphocytes to express tumor-directed chimeric antigen receptors (CAR) can produce antitumor effector cells that bypass tumor immune escape mechanisms that are due to abnormalities in protein-antigen processing and presentation. Moreover, these transgenic receptors can be directed to tumor-associated antigens that are not protein-derived. In certain embodiments of the invention, there are immune cells that are modified to comprise a CAR that targets CSPG4. In specific embodiments, the immune cells are T cells, NKT cells, or NK cells.

In particular cases, immune cells include a CAR receptor that is chimeric, non-natural and engineered at least in part by the hand of man. In particular cases, the engineered chimeric antigen receptor (CAR) has one, two, three, four, or more components, and in some embodiments the one or more components facilitate targeting or binding of the immune cell to the CSPG4-comprising cancer cell. In specific embodiments, the CAR comprises an antibody for CSPG4, part or all of one or more cytoplasmic signaling domains, and/or part or all of one or more co-stimulatory molecules, for example endodomains of co-stimulatory molecules. In specific embodiments, the antibody is a single-chain variable fragment (scFv).

In particular embodiments, the scFv is a particular scFv for CSPG4. In specific cases, the scFv for CSPG4 is scFv 763.74. The nucleotide sequence of scFv 763.74 is as follows:

```
                                            (SEQ ID NO: 1)
ATGGAGTTTGGGCTGAGCTGGCTTTTTCTTGTGGCTATTTTAAAAGGTGT

CCAGTGCTCTAGAATGGCCCAGGTCAAACTGAAGGAGTCTGGACCTGAGC

TGAAGAAGCCTGGAGAGACAGTCAAGATCTCCTGCAAGGCTTCTGGTTAT

ACCTTCACAGACTATTCAATGCACTGGGTGAAGAAGACTCCAGGAAAGGG

TTTAAAGTGGCTGGGCTGGATAAACACTGCGACTGGTGAGCCAACATATG

CAGATGACTTCAAGGGACGGTTTGCCATCTCTTTGGAAACCTCTGCCAGG

ACTGTCTATTTGCAGATCAATAATCTCAGAAATGAGGACACGGCTACATA

TTTCTGTTTTAGTTACTACGACTACTGGGGCCAAGGCACCACGGTCACCG

TCTCCTCAGGTGGGGCGGTTCAGGCGGAGGTGGCTCTGGCGGTGGCGGA

TTGGACATCAAGCTCACTCAGTCTCCATCCATCCTGTCTGTGACTCCAGG

TGAAACAGTCAGTCTTTCCTGTAGGGCCAGCCAGACTATTTACAAGAACC

TACACTGGTATCAACAGAAATCACATCGGTCTCCAAGGCTTCTCATCAAG

TATGGTTCTGATTCCATCTCTGGGATCCCCTCCAGGTTCACTGGCAGTGG

ATCAGGGACAGATTACACTCTCAATATCAACAGTGTGAAGCCCGAAGATG

AAGGAATATATTACTGTCTTCAAGGTTACAGTACACCTTGGACGTTCGGT

GGAGGGACCAAGCTGGAAATAAAACGG
```

The amino acid sequence of scFv763.74 is as follows:

```
                                            (SEQ ID NO: 2)
MEFGLSWLFLVAILKGVQCSRMAQVKLKESGPELKKPGETVKISCKASGY

TFTDYSMHWVKKTPGKGLKWLGWINTATGEPTYADDFKGRFAISLETSAR

TVYLQINNLRNEDTATYFCFSYYDYWGQGTTVTVSSGGGGSGGGGSGGGG

LDIKLTQSPSILSVTPGETVSLSCRASQTIYKNLHWYQQKSHRSPRLLIK

YGSDSISGIPSRFTGSGSGTDYTLNINSVKPEDEGIYYCLQGYSTPWTFG

GGTKLEIKR
```

In certain embodiments, the antibody is not scFv 763.74, scFv 225.28; scFv 763.74; scFv VF1-TP41.2; scFv VT80.112; scFv 653.25; scFv TP61.5, scFv D2.8.5-C4B8 scFv T8-203, scFv C21 or is not derived from their respective monoclonal antibodies. In specific embodiments, the scFv is not derived from HMW-MAA-specific mouse mAbs 149.53, 225.28, 763.74, TP61.5, VF1-TP34, or VF1-TP41.2. In particular embodiments, the scFv is not derived from the monoclonal antibody designated as TP109 American Type Culture Collection (ATCC) Accession No. PTA-9582 or is not derived from the monoclonal antibody designated as VF20-VT1.7 ATCC Accession No. PTA-9583. In particular embodiments, the scFv is not derived from the mouse monoclonal antibody 11BD-2E11-2 produced by the hybridoma deposited with ATCC as accession number PTA-5643. In certain embodiments, the scFv is not derived from the monoclonal antibodies IND-1 or IND-2 and is not produced by the hybridoma XMMME-001 or XMMME-002, deposited with ATCC as HB8759 and H88760, respectively. In particular embodiments, the scFvs utilized in methods of the disclosure comprise CDRs that differ from the heavy and light chains described in U.S. Pat. No. 8,318,162, incorporated by reference herein in its entirety. In specific embodiments, the complementarity determining region (CDR) in the scFv utilized herein differs from one in which residues 24-34, 26-32, 50-52, 50-56, 89-97, or 91-96 in the light chain variable domain of IND-1 or IND-2 are employed and also differs from one in which residues 26-32, 31-35, 50-65, 53-55, 95-102, or 96-101 in the heavy chain variable domain of IND-1 or IND-2 are employed. In particular embodiments, a scFv does not target the membrane-proximal domain of CSPG4 (amino acids 1740-2221 of CSPG4). In specific embodiments, the scFv utilized in methods of the disclosure allows for reduction in interaction of CSPG4 on its cancer cell with P-selectin, such as P-selectin present on platelets, for example.

In certain embodiments, a cytoplasmic signaling domain, such as those derived from the T cell receptor zeta-chain, is employed as at least part of the chimeric receptor in order to produce stimulatory signals for T lymphocyte proliferation and effector function following engagement of the chimeric receptor with the target antigen. Examples would include, but are not limited to, endodomains from co-stimulatory molecules such as CD28, CD27, 4-1BB, ICOS, OX40, a combination thereof, or the signaling components of cytokine receptors such as IL7 and IL15. In particular embodiments, co-stimulatory molecules are employed to enhance the activation, proliferation, and cytotoxicity of T cells produced by the CSPG4-comprising CAR after antigen engagement. In specific embodiments, the co-stimulatory molecules are CD28, OX40, and 4-1BB, for example.

The CAR may be first generation, second generation, or third generation (CAR in which signaling is provided by CD3ζ together with co-stimulation provided by CD28 and a tumor necrosis factor receptor (TNFr), such as 4-1BB or OX40), for example. The CAR may be specific for CSPG4 and it may include other CARs, such as those specific for CD19, CD20, CD22, CD138, Glypican-3, Kappa or light chain, CD30, CD33, CD123, CD38, ROR1, ErbB2, ErbB3/4, EGFR vIII, carcinoembryonic antigen, EGP2, EGP40, mesothelin, TAG72, PSMA, NKG2D ligands, B7-H6, IL-13 receptor α2, IL-11 receptor Rα, MUC1, MUC16, CA9, GD2, GD3, HMW-MAA, CD171, Lewis Y, G250/CAIX, HLA-AI MAGE A1, HLA-A2 NY-ESO-1, PSC1, folate receptor-α, CD44v7/8, 8H9, NCAM, VEGF receptors, 5T4, Fetal AchR, NKG2D ligands, or CD44v6, and other tumor-associated antigens or actionable mutations that are identified through genomic analysis and or differential expression studies of tumors, for example.

In particular cases the CAR is specific for CSPG4, and in certain embodiments, the present invention provides chimeric T cells specific for CSPG4 by joining an extracellular antigen-binding domain derived from a CSPG4-specific antibody to cytoplasmic signaling domains derived from the T-cell receptor ζ-chain, optionally with the endodomains of the exemplary costimulatory molecules CD28 and OX40, for examples. This CAR is expressed in human cells, such as human immune cells, including human T cells, and the targeting of one or more CSPG4-positive cancers is encompassed herein.

In specific embodiments, there is a hinge region between the $V_H$ and $V_L$ domains, and one can alter the length of the hinge in a variety of CSPG4-CARs. One can utilize short hinges or long hinges, in particular embodiments. In specific embodiments, the hinge is between about 10 to 25 amino acids. In specific embodiments, a full hinge is employed, such as, for example, the hinge from IgG1. In certain embodiments, part or all of the hinge of IgG1 is utilized. In certain embodiments, the hinge is rich in glycine, to impact flexibility, and/or is rich in serine and/or threonine, to impact solubility. In particular embodiments, the hinge can either connect the N-terminus of the $V_H$ with the C-terminus of the $V_L$, or vice versa. Optimization of different CSPG4-CARs may occur in vitro and/or in vivo, for example in mouse models, such as in NSG tumor-bearing mice.

In some embodiments, the CAR utilizes a transmembrane domain. In specific embodiments, the transmembrane is derived from that of CD28 or 4-1BB or CD8 alpha, for example. In other embodiments, the number and kind of co-stimulatory endodomains may differ between CSPG4 CARs. For example, the CSPG4 CAR may utilize CD28 co-stimulatory endodomain, 4-1BB co-stimulatory endodomain, or both.

In specific embodiments, the CSPG4 CAR comprises the entire IgG1 hinge and IgG1 $C_H2C_H3$ domain with the CD28 transmembrane domain and CD28 endodomain or 4-1BB endodomain. In specific embodiments, the CSPG4 CAR comprises the entire IgG1 hinge but lacks the IgG1$C_H2C_H3$ domain but comprises the CD28 transmembrane domain and CD28 endodomain or 4-1BB endodomain. In certain embodiments, the CSPG4 CAR comprises the entire IgG1 hinge but lacks the IgG1$C_H2C_H3$ domain but comprises the CD8a alpha transmembrane domain and comprises the CD28 endodomain or 4-1BB endodomain. In specific embodiments, the CSPG4 CAR comprises the full CD8a alpha stalk, including hinge and transmembrane domain, and comprises CD28 endodomain or 4-1BB endodomain. In some embodiments, the CSPG4 CAR is a third generation CAR (comprises multiple signaling domains) and further comprises CD28 and 4-1BB endodomains.

IV. Cells

Cells of the disclosure include mammalian cells, such as human cells, including immune cells that express a CSPG4-targeting CAR. In specific embodiments, the cells are engineered to express a CAR and, therefore, are not found in nature.

As used herein, the terms "cell," "cell line," and "cell culture" may be used interchangeably. All of these terms also include their progeny, which is any and all subsequent generations. It is understood that all progeny may not be identical due to deliberate or inadvertent mutations. In the context of expressing a heterologous nucleic acid sequence, "host cell" refers to a eukaryotic cell that is capable of replicating a vector and/or expressing a heterologous gene encoded by a vector. A host cell can, and has been, used as a recipient for vectors. A host cell may be "transfected" or "transformed," which refers to a process by which exogenous nucleic acid is transferred or introduced into the host cell. A transformed cell includes the primary subject cell and its progeny. As used herein, the terms "engineered" and "recombinant" cells or host cells are intended to refer to a cell into which an exogenous nucleic acid sequence, such as, for example, a vector, has been introduced. Therefore, recombinant cells are distinguishable from naturally occurring cells which do not contain a recombinantly introduced nucleic acid. In embodiments of the invention, a host cell is a T cell, including a cytotoxic T cell (also known as TC, Cytotoxic T Lymphocyte, CTL, T-Killer cell, cytolytic T cell, CD8+ T-cells or killer T cell); NK cells and NKT cells are also encompassed in the invention.

In certain embodiments, it is contemplated that RNAs or proteinaceous sequences may be co-expressed with other selected RNAs or proteinaceous sequences in the same cell, such as the same CTL. Co expression may be achieved by co-transfecting the CTL with two or more distinct recombinant vectors. Alternatively, a single recombinant vector may be constructed to include multiple distinct coding regions for RNAs, which could then be expressed in CTLs transfected with the single vector.

Some vectors may employ control sequences that allow it to be replicated and/or expressed in both prokaryotic and eukaryotic cells. One of skill in the art would further understand the conditions under which to incubate all of the above described host cells to maintain them and to permit replication of a vector. Also understood and known are techniques and conditions that would allow large-scale production of vectors, as well as production of the nucleic acids encoded by vectors and their cognate polypeptides, proteins, or peptides.

The cells can be autologous cells, syngeneic cells, allogenic cells and even in some cases, xenogeneic cells.

In many situations one may wish to be able to kill the modified CTLs, where one wishes to terminate the treatment, the cells become neoplastic, in research where the absence of the cells after their presence is of interest, and/or another event. For this purpose one can provide for the expression of certain gene products in which one can kill the modified cells under controlled conditions, such as inducible suicide genes (such as caspase 9).

In certain embodiments, the cells that express a CSPG4-targeting CAR comprise recombinant expression of heparanase, such as when there is no expression of endogenous heparanase in the cell or wherein existing expression of heparanase is overexpressed upon recombinant expression of heparanase. In specific embodiments, the cells lack endogenous heparanase expression and the modifying step restores heparanase expression or the cells have endogenous heparanase expression and the heparanase is overexpressed. Such cells may be capable of penetrating the extracellular matrix (ECM), and also exhibit improved migration through the ECM. In certain aspects, the modified cells are able to (or are able to more effectively) degrade heparin sulphate proteoglycans (main components of ECM and cell surface). In specific embodiments, the cells comprise a vector that comprises an expression construct that encodes heparanase and the vector may be viral (such as retroviral, adenoviral, or adeno-associated viral) or non-viral, such as a plasmid. The vector or expression construct that encodes heparanase may also encode the CSPG4 CAR expression construct, although they may be comprised on different expression constructs or vectors.

In specific embodiments, there are cells that harbor a polynucleotide that encodes a CSPG4 CAR and also harbor a polynucleotide that encodes one or more cytokines, such as IL-15, IL-2, IL-7, IL-4, IL-12, and/or IL-21. In some embodiments, the polynucleotide that encodes the CSPG4 CAR also encodes the one or more cytokines, although in other embodiments the CSPG4 CAR and the one or more cytokines are present on different polynucleotides.

V. Illustrative Exemplifications

By way of illustration, individuals with cancer or at risk for cancer (such as having one or more risk factors) or suspected of having cancer may be treated as follows. CTLs modified as described herein may be administered to the individual and retained for extended periods of time. The individual may receive one or more administrations of the cells. In some embodiments, the genetically modified cells are encapsulated to inhibit immune recognition and placed at the site of the tumor.

In particular cases, an individual is provided with therapeutic CTLs modified to comprise a CAR specific for CSPG4 in addition to other types of therapeutic cells. The cells may be delivered at the same time or at different times. The cells may be delivered in the same or separate formulations. The cells may be provided to the individual in separate delivery routes. The cells may be delivered by injection at a tumor site or intravenously or orally, for example. Routine delivery routes for such compositions are known in the art. Cells may be provided locally or systemically.

VI. Introduction of Constructs into CTLs

Expression vectors that encode the CSPG4 CARs can be introduced as a DNA molecule or construct, where there may be at least one marker that will allow for selection of host cells that contain the construct(s). The constructs can be prepared in conventional ways, where the genes and regulatory regions may be isolated, as appropriate, ligated, cloned in an appropriate cloning host, analyzed by restriction or sequencing, or other convenient means. Particularly, using PCR, individual fragments including all or portions of a functional unit may be isolated, where one or more mutations may be introduced using "primer repair", ligation, in vitro mutagenesis, etc., as appropriate. The construct(s) once completed and demonstrated to have the appropriate sequences may then be introduced into the CTL by any convenient means. The constructs may be integrated and packaged into non-replicating, defective viral genomes like Adenovirus, Adeno-associated virus (AAV), or Herpes simplex virus (HSV) or others, including retroviral vectors, for infection or transduction into cells. The constructs may include viral sequences for transfection, if desired. Alternatively, the construct may be introduced by fusion, electroporation, biolistics, transfection, lipofection, or the like. The host cells may be grown and expanded in culture before introduction of the construct(s), followed by the appropriate treatment for introduction of the construct(s) and integration of the construct(s). The cells are then expanded and screened by virtue of a marker present in the construct. Various markers that may be used successfully include hprt, neomycin resistance, thymidine kinase, hygromycin resistance, etc.

In some instances, one may have a target site for homologous recombination, where it is desired that a construct be integrated at a particular locus. For example,) can knock-out an endogenous gene and replace it (at the same locus or elsewhere) with the gene encoded for by the construct using materials and methods as are known in the art for homologous recombination. For homologous recombination, one may use either OMEGA or O-vectors. See, for example, Thomas and Capecchi, Cell (1987) 51, 503-512; Mansour, et al., Nature (1988) 336, 348-352; and Joyner, et al., Nature (1989) 338, 153-156.

Vectors containing useful elements such as bacterial or yeast origins of replication, selectable and/or amplifiable markers, promoter/enhancer elements for expression in prokaryotes or eukaryotes, etc. that may be used to prepare stocks of construct DNAs and for carrying out transfections are well known in the art, and many are commercially available.

VII. Administration of Cells

The exemplary T cells that have been modified with the construct(s) are then grown in culture under selective conditions and cells that are selected as having the construct may then be expanded and further analyzed, using, for example; the polymerase chain reaction for determining the presence of the construct in the host cells. Once the modified host cells have been identified, they may then be used as planned, e.g. expanded in culture or introduced into a host organism.

Depending upon the nature of the cells, the cells may be introduced into a host organism, e.g. a mammal, in a wide variety of ways. The cells may be introduced at the site of the tumor, in specific embodiments, although in alternative embodiments the cells hone to the cancer or are modified to hone to the cancer. The number of cells that are employed will depend upon a number of circumstances, the purpose for the introduction, the lifetime of the cells, the protocol to be used, for example, the number of administrations, the ability of the cells to multiply, the stability of the recombinant construct, and the like. The cells may be applied as a dispersion, generally being injected at or near the site of interest. The cells may be in a physiologically-acceptable medium.

The DNA introduction need not result in integration in every case. In some situations, transient maintenance of the DNA introduced may be sufficient. In this way, one could have a short term effect, where cells could be introduced into the host and then turned on after a predetermined time, for example, after the cells have been able to home to a particular site.

The cells may be administered as desired. Depending upon the response desired, the manner of administration, the life of the cells, the number of cells present, various protocols may be employed. The number of administrations will depend upon the factors described above at least in part.

It should be appreciated that the system is subject to many variables, such as the cellular response to the ligand, the efficiency of expression and, as appropriate, the level of secretion, the activity of the expression product, the particular need of the patient, which may vary with time and circumstances, the rate of loss of the cellular activity as a result of loss of cells or expression activity of individual cells, and the like. Therefore, it is expected that for each individual patient, even if there were universal cells which could be administered to the population at large, each patient would be monitored for the proper dosage for the individual, and such practices of monitoring a patient are routine in the art.

VIII. Nucleic Acid-Based Expression Systems

A polynucleotide encoding the CSPG4 CAR and optionally a suicide gene may comprise an expression vector. In specific embodiments, cells that harbor a polynucleotide that encodes a CSPG4 CAR also harbor a polynucleotide that encodes one or more cytokines, such as IL-15, IL-2, IL-7, IL-4, IL-12, and/or IL-21. In some embodiments, the polynucleotide that encodes the CSPG4 CAR also encodes the one or more cytokines, although in other embodiments the CSPG4 CAR and the one or more cytokines are present on different polynucleotides.

A. Vectors

The term "vector" is used to refer to a carrier nucleic acid molecule into which a nucleic acid sequence can be inserted for introduction into a cell where it can be replicated. A nucleic acid sequence can be "exogenous," which means that it is foreign to the cell into which the vector is being introduced or that the sequence is homologous to a sequence in the cell but in a position within the host cell nucleic acid in which the sequence is ordinarily not found. Vectors include plasmids, cosmids, viruses (bacteriophage, animal viruses, and plant viruses), and artificial chromosomes (e.g., YACs). One of skill in the art would be well equipped to construct a vector through standard recombinant techniques (see, for example, Maniatis et al., 1988 and Ausubel et al., 1994, both incorporated herein by reference).

The term "expression vector" refers to any type of genetic construct comprising a nucleic acid coding for a RNA capable of being transcribed. In some cases, RNA molecules are then translated into a protein, polypeptide, or peptide. In other cases, these sequences are not translated, for example, in the production of antisense molecules or ribozymes. Expression vectors can contain a variety of "control sequences," which refer to nucleic acid sequences necessary for the transcription and possibly translation of an operably linked coding sequence in a particular host cell. In addition to control sequences that govern transcription and translation, vectors and expression vectors may contain nucleic acid sequences that serve other functions as well and are described infra.

B. Promoters and Enhancers

A "promoter" is a control sequence that is a region of a nucleic acid sequence at which initiation and rate of transcription are controlled. It may contain genetic elements at which regulatory proteins and molecules may bind, such as RNA polymerase and other transcription factors, to initiate the specific transcription a nucleic acid sequence. The phrases "operatively positioned," "operatively linked," "under control," and "under transcriptional control" mean that a promoter is in a correct functional location and/or orientation in relation to a nucleic acid sequence to control transcriptional initiation and/or expression of that sequence.

A promoter generally comprises a sequence that functions to position the start site for RNA synthesis. The best known example of this is the TATA box, but in some promoters lacking a TATA box, such as, for example, the promoter for the mammalian terminal deoxynucleotidyl transferase gene and the promoter for the SV40 late genes, a discrete element overlying the start site itself helps to fix the place of initiation. Additional promoter elements regulate the frequency of transcriptional initiation. Typically, these are located in the region 30 110 bp upstream of the start site, although a number of promoters have been shown to contain functional elements downstream of the start site as well. To bring a coding sequence "under the control of" a promoter, one positions the 5' end of the transcription initiation site of the transcriptional reading frame "downstream" of (i.e., 3' of) the chosen promoter. The "upstream" promoter stimulates transcription of the DNA and promotes expression of the encoded RNA.

The spacing between promoter elements frequently is flexible, so that promoter function is preserved when elements are inverted or moved relative to one another. In the tk promoter, the spacing between promoter elements can be increased to 50 bp apart before activity begins to decline. Depending on the promoter, it appears that individual elements can function either cooperatively or independently to activate transcription. A promoter may or may not be used in conjunction with an "enhancer," which refers to a cis-acting regulatory sequence involved in the transcriptional activation of a nucleic acid sequence.

A promoter may be one naturally associated with a nucleic acid sequence, as may be obtained by isolating the 5' non-coding sequences located upstream of the coding segment and/or exon. Such a promoter can be referred to as "endogenous." Similarly, an enhancer may be one naturally associated with a nucleic acid sequence, located either downstream or upstream of that sequence. Alternatively, certain advantages will be gained by positioning the coding nucleic acid segment under the control of a recombinant or heterologous promoter, which refers to a promoter that is not normally associated with a nucleic acid sequence in its natural environment. A recombinant or heterologous enhancer refers also to an enhancer not normally associated with a nucleic acid sequence in its natural environment. Such promoters or enhancers may include promoters or enhancers of other genes, and promoters or enhancers isolated from any other virus, or prokaryotic or eukaryotic cell, and promoters or enhancers not "naturally occurring," i.e., containing different elements of different transcriptional regulatory regions, and/or mutations that alter expression. For example, promoters that are most commonly used in recombinant DNA construction include the beta-lactamase (penicillinase), lactose and tryptophan (trp) promoter systems. In addition to producing nucleic acid sequences of promoters and enhancers synthetically, sequences may be produced using recombinant cloning and/or nucleic acid amplification technology, including PCR™, in connection with the compositions disclosed herein (see U.S. Pat. Nos. 4,683,202 and 5,928,906, each incorporated herein by reference). Furthermore, it is contemplated the control sequences that direct transcription and/or expression of sequences within non-nuclear organelles such as mitochondria, chloroplasts, and the like, can be employed as well.

Naturally, it will be important to employ a promoter and/or enhancer that effectively directs the expression of the DNA segment in the organelle, cell type, tissue, organ, or organism chosen for expression. Those of skill in the art of molecular biology generally know the use of promoters, enhancers, and cell type combinations for protein expression, (see, for example Sambrook et al. 1989, incorporated herein by reference). The promoters employed may be constitutive, tissue-specific, inducible, and/or useful under the appropriate conditions to direct high level expression of the introduced DNA segment, such as is advantageous in the large-scale production of recombinant proteins and/or peptides. The promoter may be heterologous or endogenous.

Additionally any promoter/enhancer combination could also be used to drive expression. Use of a T3, T7 or SP6 cytoplasmic expression system is another possible embodiment. Eukaryotic cells can support cytoplasmic transcription from certain bacterial promoters if the appropriate bacterial polymerase is provided, either as part of the delivery complex or as an additional genetic expression construct.

The identity of tissue-specific promoters or elements, as well as assays to characterize their activity, is well known to those of skill in the art.

A specific initiation signal also may be required for efficient translation of coding sequences. These signals include the ATG initiation codon or adjacent sequences. Exogenous translational control signals, including the ATG initiation codon, may need to be provided. One of ordinary skill in the art would readily be capable of determining this and providing the necessary signals.

In certain embodiments of the invention, the use of internal ribosome entry sites (IRES) elements are used to create multigene, or polycistronic, messages, and these may be used in the invention.

Vectors can include a multiple cloning site (MCS), which is a nucleic acid region that contains multiple restriction enzyme sites, any of which can be used in conjunction with standard recombinant technology to digest the vector. "Restriction enzyme digestion" refers to catalytic cleavage of a nucleic acid molecule with an enzyme that functions only at specific locations in a nucleic acid molecule. Many of these restriction enzymes are commercially available. Use of such enzymes is widely understood by those of skill in the art. Frequently, a vector is linearized or fragmented using a restriction enzyme that cuts within the MCS to enable exogenous sequences to be ligated to the vector. "Ligation" refers to the process of forming phosphodiester bonds between two nucleic acid fragments, which may or may not be contiguous with each other. Techniques involving restriction enzymes and ligation reactions are well known to those of skill in the art of recombinant technology.

Splicing sites, termination signals, origins of replication, and selectable markers may also be employed.

C. Plasmid Vectors

In certain embodiments, a plasmid vector is contemplated for use to transform a host cell. In general, plasmid vectors containing replicon and control sequences which are derived from species compatible with the host cell are used in connection with these hosts. The vector ordinarily carries a replication site, as well as marking sequences which are capable of providing phenotypic selection in transformed cells. In a non-limiting example, *E. coli* is often transformed using derivatives of pBR322, a plasmid derived from an *E. coli* species. pBR322 contains genes for ampicillin and tetracycline resistance and thus provides easy means for identifying transformed cells. The pBR plasmid, or other microbial plasmid or phage must also contain, or be modified to contain, for example, promoters which can be used by the microbial organism for expression of its own proteins.

In addition, phage vectors containing replicon and control sequences that are compatible with the host microorganism can be used as transforming vectors in connection with these hosts. For example, the phage lambda GEM™ 11 may be utilized in making a recombinant phage vector which can be used to transform host cells, such as, for example, *E. coli* LE392.

Further useful plasmid vectors include pIN vectors (Inouye et al., 1985); and pGEX vectors, for use in generating glutathione S transferase (GST) soluble fusion proteins for later purification and separation or cleavage. Other suitable fusion proteins are those with □ galactosidase, ubiquitin, and the like.

Bacterial host cells, for example, *E. coli*, comprising the expression vector, are grown in any of a number of suitable media, for example, LB. The expression of the recombinant protein in certain vectors may be induced, as would be understood by those of skill in the art, by contacting a host cell with an agent specific for certain promoters, e.g., by adding IPTG to the media or by switching incubation to a higher temperature. After culturing the bacteria for a further period, generally of between 2 and 24 h, the cells are collected by centrifugation and washed to remove residual media.

D. Viral Vectors

The ability of certain viruses to infect cells or enter cells via receptor mediated endocytosis, and to integrate into host cell genome and express viral genes stably and efficiently have made them attractive candidates for the transfer of foreign nucleic acids into cells (e.g., mammalian cells). Components of the present invention may be a viral vector that encodes one or more CARs of the invention. Non-limiting examples of virus vectors that may be used to deliver a nucleic acid of the present invention are described below.

1. Adenoviral Vectors

A particular method for delivery of the nucleic acid involves the use of an adenovirus expression vector. Although adenovirus vectors are known to have a low capacity for integration into genomic DNA, this feature is counterbalanced by the high efficiency of gene transfer afforded by these vectors. "Adenovirus expression vector" is meant to include those constructs containing adenovirus sequences sufficient to (a) support packaging of the construct and (b) to ultimately express a tissue or cell specific construct that has been cloned therein. Knowledge of the genetic organization or adenovirus, a 36 kb, linear, double stranded DNA virus, allows substitution of large pieces of adenoviral DNA with foreign sequences up to 7 kb (Grunhaus and Horwitz, 1992).

2. AAV Vectors

The nucleic acid may be introduced into the cell using adenovirus assisted transfection. Increased transfection efficiencies have been reported in cell systems using adenovirus coupled systems (Kelleher and Vos, 1994; Cotten et al., 1992; Curiel, 1994). Adeno associated virus (AAV) is an attractive vector system for use in the cells of the present invention as it has a high frequency of integration and it can infect nondividing cells, thus making it useful for delivery of genes into mammalian cells, for example, in tissue culture (Muzyczka, 1992) or in vivo. AAV has a broad host range for infectivity (Tratschin et al., 1984; Laughlin et al., 1986; Lebkowski et al., 1988; McLaughlin et al., 1988). Details concerning the generation and use of rAAV vectors are described in U.S. Pat. Nos. 5,139,941 and 4,797,368, each incorporated herein by reference.

3. Retroviral Vectors

Retroviruses are useful as delivery vectors because of their ability to integrate their genes into the host genome, transferring a large amount of foreign genetic material, infecting a broad spectrum of species and cell types and of being packaged in special cell lines (Miller, 1992).

In order to construct a retroviral vector, a nucleic acid (e.g., one encoding the desired sequence) is inserted into the viral genome in the place of certain viral sequences to produce a virus that is replication defective. In order to produce virions, a packaging cell line containing the gag, pol, and env genes but without the LTR and packaging components is constructed (Mann et al., 1983). When a recombinant plasmid containing a cDNA, together with the retroviral LTR and packaging sequences is introduced into a special cell line (e.g., by calcium phosphate precipitation for example), the packaging sequence allows the RNA transcript of the recombinant plasmid to be packaged into viral particles, which are then secreted into the culture media (Nicolas and Rubenstein, 1988; Temin, 1986; Mann et al., 1983). The media containing the recombinant retroviruses is then collected, optionally concentrated, and used for gene transfer. Retroviral vectors are able to infect a broad variety of cell types. However, integration and stable expression require the division of host cells (Paskind et al., 1975).

Lentiviruses are complex retroviruses, which, in addition to the common retroviral genes gag, pol, and env, contain other genes with regulatory or structural function. Lentiviral vectors are well known in the art (see, for example, Naldini et al., 1996; Zufferey et al., 1997; Blomer et al., 1997; U.S. Pat. Nos. 6,013,516 and 5,994,136). Some examples of lentivirus include the Human Immunodeficiency Viruses: HIV-1, HIV-2 and the Simian Immunodeficiency Virus: SIV. Lentiviral vectors have been generated by multiply attenuating the HIV virulence genes, for example, the genes env, vif, vpr, vpu and nef are deleted making the vector biologically safe.

Recombinant lentiviral vectors are capable of infecting non-dividing cells and can be used for both in vivo and ex vivo gene transfer and expression of nucleic acid sequences. For example, recombinant lentivirus capable of infecting a non-dividing cell wherein a suitable host cell is transfected with two or more vectors carrying the packaging functions, namely gag, pol and env, as well as rev and tat is described in U.S. Pat. No. 5,994,136, incorporated herein by reference. One may target the recombinant virus by linkage of the envelope protein with an antibody or a particular ligand for targeting to a receptor of a particular cell-type. By inserting a sequence (including a regulatory region) of interest into the viral vector, along with another gene which encodes the ligand for a receptor on a specific target cell, for example, the vector is now target-specific.

4. Other Viral Vectors

Other viral vectors may be employed as vaccine constructs in the present invention. Vectors derived from viruses such as vaccinia virus (Ridgeway, 1988; Baichwal and Sugden, 1986; Coupar et al., 1988), sindbis virus, cytomegalovirus and herpes simplex virus may be employed. They offer several attractive features for various mammalian cells (Friedmann, 1989; Ridgeway, 1988; Baichwal and Sugden, 1986; Coupar et al., 1988; Horwich et al., 1990).

E. Delivery Using Modified Viruses

A nucleic acid to be delivered may be housed within an infective virus that has been engineered to express a specific binding ligand. The virus particle will thus bind specifically to the cognate receptors of the target cell and deliver the contents to the cell. A novel approach designed to allow specific targeting of retrovirus vectors was developed based on the chemical modification of a retrovirus by the chemical addition of lactose residues to the viral envelope. This modification can permit the specific infection of hepatocytes via sialoglycoprotein receptors.

Another approach to targeting of recombinant retroviruses was designed in which biotinylated antibodies against a retroviral envelope protein and against a specific cell receptor were used. The antibodies were coupled via the biotin components by using streptavidin (Roux et al., 1989). Using antibodies against major histocompatibility complex class I and class II antigens, they demonstrated the infection of a variety of human cells that bore those surface antigens with an ecotropic virus in vitro (Roux et al., 1989).

F. Vector Delivery and Cell Transformation

Suitable methods for nucleic acid delivery for transfection or transformation of cells are known to one of ordinary skill in the art. Such methods include, but are not limited to, direct delivery of DNA such as by ex vivo transfection, by injection, and so forth. Through the application of techniques known in the art, cells may be stably or transiently transformed.

G. Ex Vivo Transformation

Methods for transfecting eukaryotic cells and tissues removed from an organism in an ex vivo setting are known to those of skill in the art. Thus, it is contemplated that cells or tissues may be removed and transfected ex vivo using nucleic acids of the present invention. In particular aspects, the transplanted cells or tissues may be placed into an organism. In certain facets, a nucleic acid is expressed in the transplanted cells.

IX. Kits of the Invention

Any of the CSPG4 CAR compositions described herein may be comprised in a kit, including nucleic acids, proteins, peptides, and/or cells. In a non-limiting example, one or more cells for use in cell therapy and/or the reagents to generate one or more cells for use in cell therapy that harbors recombinant expression vectors may be comprised in a kit. Polynucleotides that encodes the CSPG4 CAR or portions thereof may be included in the kit. The kit components are provided in suitable container means.

Some components of the kits may be packaged either in aqueous media or in lyophilized form. The container means of the kits will generally include at least one vial, test tube, flask, bottle, syringe or other container means, into which a component may be placed, and preferably, suitably aliquoted. Where there are more than one component in the kit, the kit also will generally contain a second, third or other additional container into which the additional components may be separately placed. However, various combinations of components may be comprised in a vial. The kits of the present invention also will typically include a means for containing the components in close confinement for commercial sale. Such containers may include injection or blow molded plastic containers into which the desired vials are retained.

When the components of the kit are provided in one and/or more liquid solutions, the liquid solution is an aqueous solution, with a sterile aqueous solution being particularly useful. In some cases, the container means may itself be a syringe, pipette, and/or other such like apparatus, from which the formulation may be applied to an infected area of the body, injected into an animal, and/or even applied to and/or mixed with the other components of the kit.

However, the components of the kit may be provided as dried powder(s). When reagents and/or components are provided as a dry powder, the powder can be reconstituted by the addition of a suitable solvent. It is envisioned that the solvent may also be provided in another container means. The kits may also comprise a second container means for containing a sterile, pharmaceutically acceptable buffer and/ or other diluent.

In particular embodiments of the invention, cells that are to be used for cell therapy are provided in a kit, and in some cases the cells are essentially the sole component of the kit. The kit may comprise reagents and materials to make the desired cell. In specific embodiments, the reagents and materials include primers for amplifying desired sequences, nucleotides, suitable buffers or buffer reagents, salt, and so forth, and in some cases the reagents include vectors and/or DNA that encodes a CAR as described herein and/or regulatory elements therefor.

In particular embodiments, there are one or more apparatuses in the kit suitable for extracting one or more samples from an individual. The apparatus may be a syringe, scalpel, and so forth. One or more reagents and/or apparatuses for diagnosis of cancer may be included in the kit, including for blood tests, sample extraction, blood extraction, tumor marker tests (such as particular antibodies), and so forth.

In some cases of the invention, the kit, in addition to cell therapy embodiments, also includes a second cancer therapy, such as chemotherapy, hormone therapy, and/or immunotherapy, for example. The kit(s) may be tailored to a particular cancer for an individual and comprise respective second cancer therapies for the individual.

X. Combination Therapy

In certain embodiments of the invention, methods of the present invention for clinical aspects are combined with other agents effective in the treatment of hyperproliferative disease, such as anti-cancer agents. An "anti-cancer" agent is capable of negatively affecting cancer in a subject, for example, by killing cancer cells, inducing apoptosis in cancer cells, reducing the growth rate of cancer cells, reducing the incidence or number of metastases, reducing tumor size, inhibiting tumor growth, reducing the blood supply to a tumor or cancer cells, promoting an immune response against cancer cells or a tumor, preventing or inhibiting the progression of cancer, or increasing the lifespan of a subject with cancer. More generally, these other compositions would be provided in a combined amount effective to kill or inhibit proliferation of the cell. This process may involve contacting the cancer cells with the expression construct and the agent(s) or multiple factor(s) at the same time. This may be achieved by contacting the cell with a single composition or pharmacological formulation that includes both agents, or by contacting the cell with two distinct compositions or formulations, at the same time, wherein one composition includes the expression construct and the other includes the second agent(s).

Tumor cell resistance to chemotherapy and radiotherapy agents represents a major problem in clinical oncology. One goal of current cancer research is to find ways to improve the efficacy of chemo- and radiotherapy by combining it with gene therapy. For example, the herpes simplex-thymidine kinase (HS-tK) gene, when delivered to brain tumors by a retroviral vector system, successfully induced susceptibility to the antiviral agent ganciclovir (Culver, et al., 1992). In the context of the present invention, it is contemplated that cell therapy could be used similarly in conjunction with chemotherapeutic, radiotherapeutic, or immunotherapeutic intervention, in addition to other pro-apoptotic or cell cycle regulating agents.

Alternatively, the present inventive therapy may precede or follow the other agent treatment by intervals ranging from minutes to weeks. In embodiments where the other agent and present invention are applied separately to the individual, one would generally ensure that a significant period of time did not expire between the time of each delivery, such that the agent and inventive therapy would still be able to exert an advantageously combined effect on the cell. In such instances, it is contemplated that one may contact the cell with both modalities within about 12-24 h of each other and, more preferably, within about 6-12 h of each other. In some situations, it may be desirable to extend the time period for treatment significantly, however, where several d (2, 3, 4, 5, 6 or 7) to several wk (1, 2, 3, 4, 5, 6, 7 or 8) lapse between the respective administrations.

Various combinations may be employed, present invention is "A" and the secondary agent, such as radio- or chemotherapy, is "B":

| | | | | | |
|---|---|---|---|---|---|
| A/B/A | B/A/B | B/B/A | A/A/B | A/B/B | B/A/A |
| A/B/B/B | B/A/B/B | B/B/A/B | B/B/A/B | A/A/B/B | A/B/A/B |
| A/B/B/A | B/B/A/A | B/A/B/A | B/A/A/B | A/A/A/B | B/A/A/A |
| A/B/A/A | A/A/B/A | | | | |

It is expected that the treatment cycles would be repeated as necessary. It also is contemplated that various standard therapies, as well as surgical intervention, may be applied in combination with the inventive cell therapy.

A. Chemotherapy

Cancer therapies also include a variety of combination therapies with both chemical and radiation based treatments. Combination chemotherapies include, for example, abraxane, altretamine, docetaxel, herceptin, methotrexate, novantrone, zoladex, cisplatin (CDDP), carboplatin, procarbazine, mechlorethamine, cyclophosphamide, camptothecin, ifosfamide, melphalan, chlorambucil, busulfan, nitrosurea, dactinomycin, daunorubicin, doxorubicin, bleomycin, plicomycin, mitomycin, etoposide (VP16), tamoxifen, raloxifene, estrogen receptor binding agents, taxol, gemcitabien, navelbine, farnesyl-protein tansferase inhibitors, transplatinum, 5-fluorouracil, vincristin, vinblastin and methotrexate, or any analog or derivative variant of the foregoing and also combinations thereof.

In specific embodiments, chemotherapy for the individual is employed in conjunction with the invention, for example before, during and/or after administration of the invention.

B. Radiotherapy

Other factors that cause DNA damage and have been used extensively include what are commonly known as γ-rays, X-rays, and/or the directed delivery of radioisotopes to tumor cells. Other forms of DNA damaging factors are also contemplated such as microwaves and UV-irradiation. It is most likely that all of these factors effect a broad range of damage on DNA, on the precursors of DNA, on the replication and repair of DNA, and on the assembly and maintenance of chromosomes. Dosage ranges for X-rays range from daily doses of 50 to 200 roentgens for prolonged periods of time (3 to 4 wk), to single doses of 2000 to 6000 roentgens. Dosage ranges for radioisotopes vary widely, and depend on the half-life of the isotope, the strength and type of radiation emitted, and the uptake by the neoplastic cells.

The terms "contacted" and "exposed," when applied to a cell, are used herein to describe the process by which a therapeutic construct and a chemotherapeutic or radiotherapeutic agent are delivered to a target cell or are placed in direct juxtaposition with the target cell. To achieve cell killing or stasis, both agents are delivered to a cell in a combined amount effective to kill the cell or prevent it from dividing.

C. Immunotherapy

Immunotherapeutics generally rely on the use of immune effector cells and molecules to target and destroy cancer cells. The immune effector may be, for example, an antibody specific for some marker on the surface of a tumor cell. The antibody alone may serve as an effector of therapy or it may recruit other cells to actually effect cell killing. The antibody also may be conjugated to a drug or toxin (chemotherapeutic, radionuclide, ricin A chain, cholera toxin, pertussis toxin, etc.) and serve merely as a targeting agent. Alternatively, the effector may be a lymphocyte carrying a surface molecule that interacts, either directly or indirectly, with a tumor cell target. Various effector cells include cytotoxic T cells and NK cells.

Immunotherapy other than the inventive therapy described herein could thus be used as part of a combined therapy, in conjunction with the present cell therapy. The general approach for combined therapy is discussed below. Generally, the tumor cell must bear some marker that is amenable to targeting, i.e., is not present on the majority of other cells. Many tumor markers exist and any of these may be suitable for targeting in the context of the present invention. Common tumor markers include carcinoembryonic antigen, prostate specific antigen, urinary tumor associated antigen, fetal antigen, tyrosinase (p97), gp68, TAG-72, HMFG, Sialyl Lewis Antigen, MucA, MucB, PLAP, estrogen receptor, laminin receptor, erb B and p155.

D. Genes

In yet another embodiment, the secondary treatment is a gene therapy in which a therapeutic polynucleotide is administered before, after, or at the same time as the present invention clinical embodiments. A variety of expression products are encompassed within the invention, including inducers of cellular proliferation, inhibitors of cellular proliferation, or regulators of programmed cell death.

E. Surgery

Approximately 60% of persons with cancer will undergo surgery of some type, which includes preventative, diagnostic or staging, curative and palliative surgery. Curative surgery is a cancer treatment that may be used in conjunction with other therapies, such as the treatment of the present invention, chemotherapy, radiotherapy, hormonal therapy, gene therapy, immunotherapy and/or alternative therapies.

Curative surgery includes resection in which all or part of cancerous tissue is physically removed, excised, and/or destroyed. Tumor resection refers to physical removal of at least part of a tumor. In addition to tumor resection, treatment by surgery includes laser surgery, cryosurgery, electrosurgery, and miscopically controlled surgery (Mohs' surgery). It is further contemplated that the present invention may be used in conjunction with removal of superficial cancers, precancers, or incidental amounts of normal tissue.

Upon excision of part of all of cancerous cells, tissue, or tumor, a cavity may be formed in the body. Treatment may be accomplished by perfusion, direct injection or local application of the area with an additional anti-cancer therapy. Such treatment may be repeated, for example, every 1, 2, 3, 4, 5, 6, or 7 days, or every 1, 2, 3, 4, and 5 weeks or every 1, 2, 3, 4, 5, 6, 7, 8, 9, 10, 11, or 12 months. These treatments may be of varying dosages as well.

F. Other Agents

It is contemplated that other agents may be used in combination with the present invention to improve the therapeutic efficacy of treatment. These additional agents include immunomodulatory agents, agents that affect the upregulation of cell surface receptors and GAP junctions, cytostatic and differentiation agents, inhibitors of cell adhesion, or agents that increase the sensitivity of the hyperproliferative cells to apoptotic inducers. Immunomodulatory agents include tumor necrosis factor; interferon alpha, beta, and gamma; IL-2 and other cytokines; F42K and other cytokine analogs; or MIP-1, MIP-1beta, MCP-1, RANTES, and other chemokines. It is further contemplated that the upregulation of cell surface receptors or their ligands such as Fas/Fas ligand, DR4 or DR5/TRAIL would potentiate the apoptotic inducing abilities of the present invention by establishment of an autocrine or paracrine effect on hyperproliferative cells. Increases intercellular signaling by elevating the number of GAP junctions would increase the anti-hyperproliferative effects on the neighboring hyperproliferative cell population. In other embodiments, cytostatic or differentiation agents can be used in combination with the present invention to improve the anti-hyerproliferative efficacy of the treatments. Inhibitors of cell adhesion are contemplated to improve the efficacy of the present invention. Examples of cell adhesion inhibitors are focal adhesion kinase (FAKs) inhibitors and Lovastatin. It is further contemplated that other agents that increase the sensitivity of a hyperproliferative cell to apoptosis, such as the antibody c225, could be used in combination with the present invention to improve the treatment efficacy.

EXAMPLES

The following examples are included to demonstrate certain embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

MCSP-Chimeric Antigen Receptor (CAR)-Redirected T Cells Target Multiple Solid Tumors Melanoma-associated chondroitin sulphate proteoglycan (MCSP, also known as CSPG4) participates in tumor migration, angiogenesis and metastasis and is frequently overexpressed in tumors that develop and require these functions to survive. Taking into consideration its broad expression in cancer cells, its limited expression in normal tissues (basal cells of epidermis) and its pivotal role in tumor survival, targeting this antigen with CAR-redirected T cells offers a useful therapeutic approach for several solid tumors. As described in the Examples to follow, second generation CAR (encoding the CD28 costimulatory endodomain, as an example) targeting MCSP (CAR.MCSP) was therefore constructed in a retroviral vector. After transduction, T lymphocytes (n=4) stably and efficiently expressed the CAR (65%-88%) and lysed the melanoma cells SEMNA significantly better (59%±6%) than control T cells (11%±8%) even at the 5:1 effector-to-target ratio in $^{51}$Cr release assays. Furthermore, in long-term co-culture assays, CAR.MCSP$^+$ T cells efficiently and consistently eliminated several MCSP$^+$ targets including melanoma (SEMNA and CLB, residual tumors: 0.1%±0.06% and 0.1%±0.1, respectively), mesothelioma (PH1 and MILL: 3.8%±3.1%; 3.2%±5%), head and neck carcinoma (PCI-30, 0.5%±0.5%), and basal breast carcinoma (UACC-812 and MDA-MB-231: 5.7%±6.1%; 3.1%±2.5%, respectively) while having no effect on a MCSP$^-$ targets (38%±10%). As expected all tumor cells expanded in co-culture with control T cells. The antitumor activity of CAR.MCSP$^+$ T cells was paralleled by release of Th1 cytokines, such as IL2 (from 6±10 pg/µL to 190±98 pg/µL) and IFNg (from 105±48 pg/µL to 3710±975 pg/µL) upon coculture with different MCSP$^+$ tumors. Both CAR.MCSP transgenic CD4$^+$ and CD8$^+$ cells proliferated in response to SEMNA tumor cells as compared to control T cells, as assessed by CFSE dilution assays. A third generation CAR encoding CD28 and 4-1BB endodomains (as examples) was also produced. However, since this construct did not show superior function in at least certain cases in vitro as compared to the CD28 endodomain, the latter was selected for the following in vivo experiments. Using NSG mice (n=10/group) either melanoma (SEMNA) or head and neck carcinoma (PCI-30) or basal breast carcinoma (UACC-812) cells were engrafted s.c. Across all tumor models, mice treated with CAR.MCSP$^+$ T lymphocytes consistently showed tumor control (753 mm$^3$±350 mm$^3$; 18.5 mm$^3$±10 mm$^3$; 28 mm$^3$±13 mm$^3$) as compared to mice receiving control T lymphocytes (7126 mm$^3$±2500 mm$^3$; 190 mm$^3$±75 mm$^3$; 166 mm$^3$±64 mm$^3$) by days 40-50 post tumor engraftment. In summary, CAR.MCSP-redirected T cells can be used for the treatment of a variety of solid tumors.

Example 2

Exemplary Materials and Methods

Cell Lines.

The previously described SENMA, CLB and P1143 tumor cell lines were generated in the laboratory from melanoma biopsies. MDA-MB-231 was originally obtained from American Type Culture Collection (ATCC) and authenticated by the analysis of short tandem repeat sequences performed at MD Anderson Cancer Center, Texas, USA. UACC-812, PCI-30 and PHI cell lines were obtained and these cells, when maintained in culture for several passages, retained the same phenotypic expression of CSPG4 as the early cell passages. Previously described melanoma cell lines PLAODE, NE-18732, NE-18588, NE-8959, NE-4405 and NE-371952 were only used to confirm the expression of CSPG4 in a broad array of melanoma cell lines. All these cells, including SENMA, CLB, and P1143, when maintained in culture for several passages, retained the same phenotypic expression of CSPG4 as the early cell passages. SENMA, CLB, UACC-812, MDA-MB-231, and PCI-30 cell lines were cultured in DMEM (Invitrogen Grand Island, N.Y.) or RPMI 1640 (P1143, UACC-812, and PHI) (Cambrex, East Rutherford, N.J.) medium supplemented with 10% heat inactivated fetal calf serum (FCS) (HyClone, Thermo Fisher Scientific Inc., Wyman, Mass.), 200 IU/mL penicillin, 200 mg/mL streptomycin (Invitrogen), and 2 mmol/L GlutaMAX (Invitrogen) at 37° C. in a 5% $CO_2$ atmosphere. Tumor cell lines were transduced with a gamma retroviral vector encoding eGFP to obtain GFP+ tumor cells (>98% GFP+). Primary epithelial cells from normal small airway, kidney and prostate were purchased from ATCC and kept in culture according to ATCC recommendation.

Tissue Microarrays and Immunohistochemistry (IHC).

Antigen retrieval was performed by placing the samples in 1× Dako Citrate Buffer followed by incubation at 90° C. in a pressure cooker for 45 minutes. After blocking with normal goat serum diluted in Tris-Buffered Saline, samples were incubated with the CSPG4 mAb (Abcam, Anti-NG2 antibody [LHM 2], ref #ab104535) (1:300 dilution) either overnight at 4° C. or at room temperature for 1 hour. Detection of CSPG4 was then assessed using the VECTASTAIN® ABC kit (Vector Laboratories, Inc. ref #PK-4001) following the manufacturer's protocol. Tissue arrays were obtained from Cybrdi Inc (Rockville, Md.) for breast cancer (CC08-10-001) and HNSCC (CC34-01-001), while melanoma (ME2082b), neuroblastoma (MC602), mesothelioma (T392), and normal tissue (FDA 808b) arrays were obtained from US Biomax, Inc. (Rockville, Md.). Each array contained a range of 4 to 192 cores of tumor or 5 to 18 cores of normal tissue samples in duplicate, triplicate or quadruplicate in the case of mesothelioma. Expression of CSPG4 in tumor cells was scored in blind fashion by the pathologist Dr Michael Ittmann based on both intensity (0-3+) and extent of staining (1-3+). A multiplicative staining score was calculated by multiplying the intensity and extent scores to yield scores on a 10 point scale from 0-9. In microarrays with multiple cores per patient, the individual scores were averaged to obtain a final score. In some cores, tumor was not identified due to artifacts. In the vast majority of cases, IHC showed uniform staining (3+) within a given core and in most cases cores from different patients were highly concordant. Areas of necrosis or acellular keratin were not included in the scoring. Cases were divided based on staining scores into three groups: negative/weak (0-3), moderate (4-6) or strong (7-9).

Generation of the CSPG4-Specific CAR and Transduction of T Lymphocytes.

The hybridoma 763.74 was generated from a BALB/c mouse immunized with cultured human melanoma cells. The scFv 763.74 was isolated from the hybridoma and then cloned in frame with the human IgG1-CH2CH3 domains, the CD28 costimulatory endodomain and the CD3ζ chain into the SFG retroviral backbone (CAR.CSPG4), as previously described. The control CAR specific for the CD19 antigen (CAR.CD19) has been previously described.

Transient retroviral supernatant was generated by co-transfection of 293T cells with the RD114 envelope (RDF plasmid), the MoMLV gag-pol (PegPam3-e plasmid) and the retroviral vector, as previously described. For the generation of CAR-T cells, peripheral blood mononuclear cells (PBMCs) were isolated from buffy coat preparations (Gulf Coast Regional Blood Center, Houston, Tex.) using Ficoll-Paque (Amersham Biosciences, Piscataway, N.J.). PBMCs were activated with OKT3 and CD28 (BD Biosciences PharMingen, San Diego, Calif.) mAbs, transduced with the retroviral supernatant by day 3 of culture and then expanded in complete medium containing 45% RPMI 1640 and 45% Click's medium (Irvine Scientific, Santa Ana, Calif., USA) supplemented with 10% FCS, 100 IU/mL penicillin, 100 mg/mL streptomycin, and 2 mmol/L GlutaMAX. Cells were fed with IL-2 (50 U/mL) (PeproTech; Rocky Hill, N.J.) twice a week for 2 weeks.

Flow Cytometry.

Conjugated CD3, CD4, CD8, CD45RO, CD62L and CCR7 mAbs (BD Biosciences) were used to identify T lymphocytes, while the CSPG4 mAb (Miltenyi-Biotech Inc, Auburn, Calif.) was used to label tumor cells. CAR expression in T lymphocytes was assessed using an antibody recognizing the human IgG1-CH$_2$CH$_3$ fragment (Jackson ImmunoResearch, West Grove, PN). Analyses were performed on a FACsCaliber flow cytometer using the BDFACs CellQuestPro software (BD Biosciences, San Jose, Calif.).

Cytotoxicity and Co-Culture Assays.

The cytotoxic activity of control and CAR.CSPG4+ T lymphocytes was determined using a standard $^{51}$Cr release assay at different effector-to-target (E:T) (40:1, 20:1, 10:1 and 5:1) ratios using a gamma counter (Perkin-Elmer, Waltham, Mass.)(Vera et al., 2006). For the co-culture experiments, control and CAR.CSPG4+ T lymphocytes were plated at 1×10$^6$ cells/well in 24-well plates at different E:T ratios according to the kinetic growth of each tumor cell line. Tumor cell lines with a slow kinetic growth were plated at higher tumor ratio (T cells:tumor cells 3:1) compared to tumor cell lines with a fast kinetic growth (T cells: tumor cells 5:1). Supernatant was collected at 24 hours of culture to measure IFNγ and IL-2 release using specific ELISAs (R&D system, Minneapolis, Minn.). Following 72 hours of culture at 37° C., adherent tumor cells and T cells were collected and residual tumor cells and T cells assessed by FACs analysis based on GFP and CD3 expression, respectively.

Carboxyfluorescein Diacetate Succinimidyl Ester (CFSE) Assay.

One week post transduction, control and CAR.CSPG4$^+$ T lymphocytes were labeled with 1.5 µmol/L CFSE (Invitrogen) and plated with irradiated tumor target (SENMA) at an E:T ratio of 5:1. CFSE dilution was measured on CD4$^+$ and CD8$^+$ cells by flow cytometry by day 4 of co-culture.

Xenogenic Mouse Models.

In vivo experiments were performed in accordance with Baylor College of Medicine's Animal Husbandry guidelines. Antitumor activity of control and CAR.CSPG4$^+$ T lymphocytes was evaluated using NOG/SCID/γc$^{-/-}$ mice (Jackson Lab, Bar Harbor, Me.) engrafted with tumor cells. Eight to 9 week old mice were subcutaneously injected with 0.5×10$^6$ SENMA, 3×10$^6$ UACC-812 or 3×106 PCI-30 cells resuspended in Matrigel (BD Biosciences, San Jose, Calif.). On days 4, 6, and 8 following tumor cell injection, 1×10$^7$ control or CAR.CSPG4+ T lymphocytes were injected i.v. by tail vain. In summary, for the melanoma xenograft model 3 different preparations of CAR.CSPG4 T cells were generated from 3 different donors. Three doses, given two days apart, of 1×10$^7$ were infused i.v. into 5 mice per group. In total, 15 animals were treated for each group. The endpoint of the experiment was to examine differences in tumor volume up to day 30-post tumor injection. For the xenograft models of breast cancer and HNSCC 2 different preparations of T cells generated from 2 different donors were used. Two doses, given two days apart, of 1×10$^7$ were infused i.v. into 5 mice per group. In total, 10 animals were treated per group. In all tumor models, mice were sacrificed at 30 days or in accordance with institution's guidelines for the handling of sick animals. Weekly manual caliper measurements were performed post-treatment to evaluate tumor growth. Tumor volume was calculated using the modified ellipsoidal formula: tumor volume (mm$^3$)=(width)$^2$×length/2.

Statistical Analysis.

In vitro data are presented as mean±standard deviation (SD) and a paired student's t-test was used to determine statistical significance. The in vivo data are presented as mean±standard error of the mean (SEM) and a paired student's t-test was used to identify significant differences between CAR-treated and control-treated groups. Public gene expression profiling datasets of human tumors were queried for CSPG4, including data from The Cancer Genome Atlas (TCGA Data Portal; http://tcga-data.nci.nih.gov/tcga), Bittner multi-cancer dataset (unpublished, from www.oncomine.org) and GeneAtlas U133A data set (http://niogps.org).

Example 3

CSPG4 is Expressed on a Variety of Solid Tumors

Figure 1:
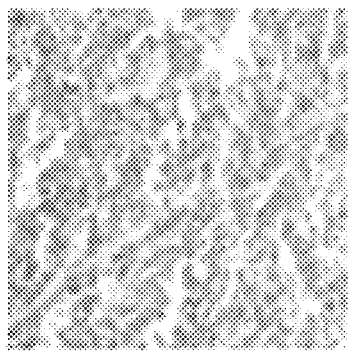
FIG. 1. CSPG4 expression in primary solid tumors and tumor-derived cell lines. Panel A. Representative immunohistochemistry (IHC) and scoring of analyzed solid tumor tissue arrays. Representative melanoma and breast carcinoma samples are shown at 200× magnification. Panel B. Scoring summary of a panel of solid tumors which includes melanoma, breast carcinoma (Breast Calif.), HNSCC, neuroblastoma (NeuroB) and mesothelioma (MesoT). Panel C. CSPG4 mRNA expression by TCGA in a variety of solid tumors. Box plots show median, 25%/75% range, 5%/95% range, and minimum/maximum. Panel D. CSPG4 mRNA expression analysis, comparing tumor versus corresponding normal tissues, for astrocytoma/glioblastoma (GBM), HNSCC, clear cell renal carcinoma, and melanoma. Indicated P-values were calculated by t-test. Panel E. CSPG4 expression in the indicated array of melanoma cell lines as assessed by flow cytometry (FACS). Panel F. FACS analysis of CSPG4 expression in the selected mesothelioma (MILL and PHI), HNSCC (PCI-30), and breast cancer-derived (MDA-MB-231 and UACC-812) cells lines. Dotted and bold lines indicate isotype and CSPG4 mAbs, respectively.
Figure 1:
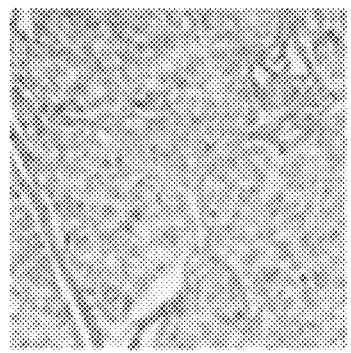
Figure 1:
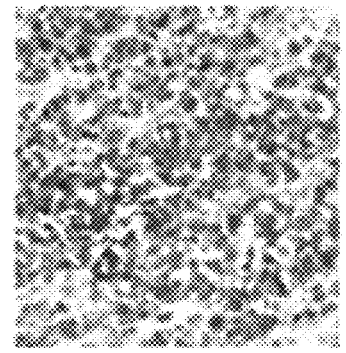
Figure 1:
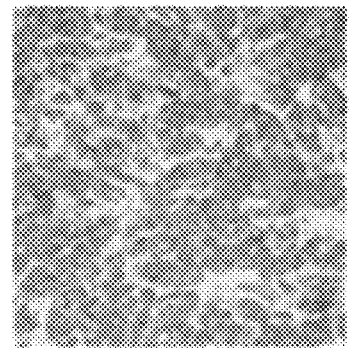
Figure 1:
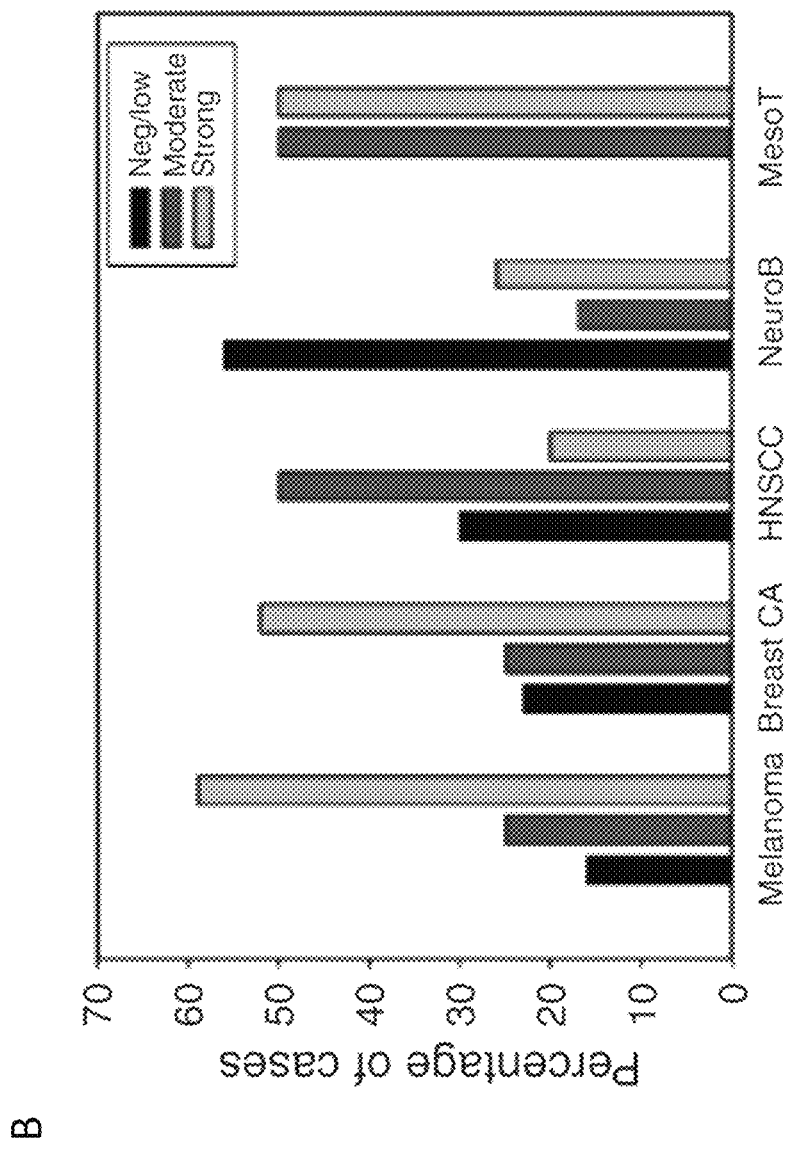
Figure 1:
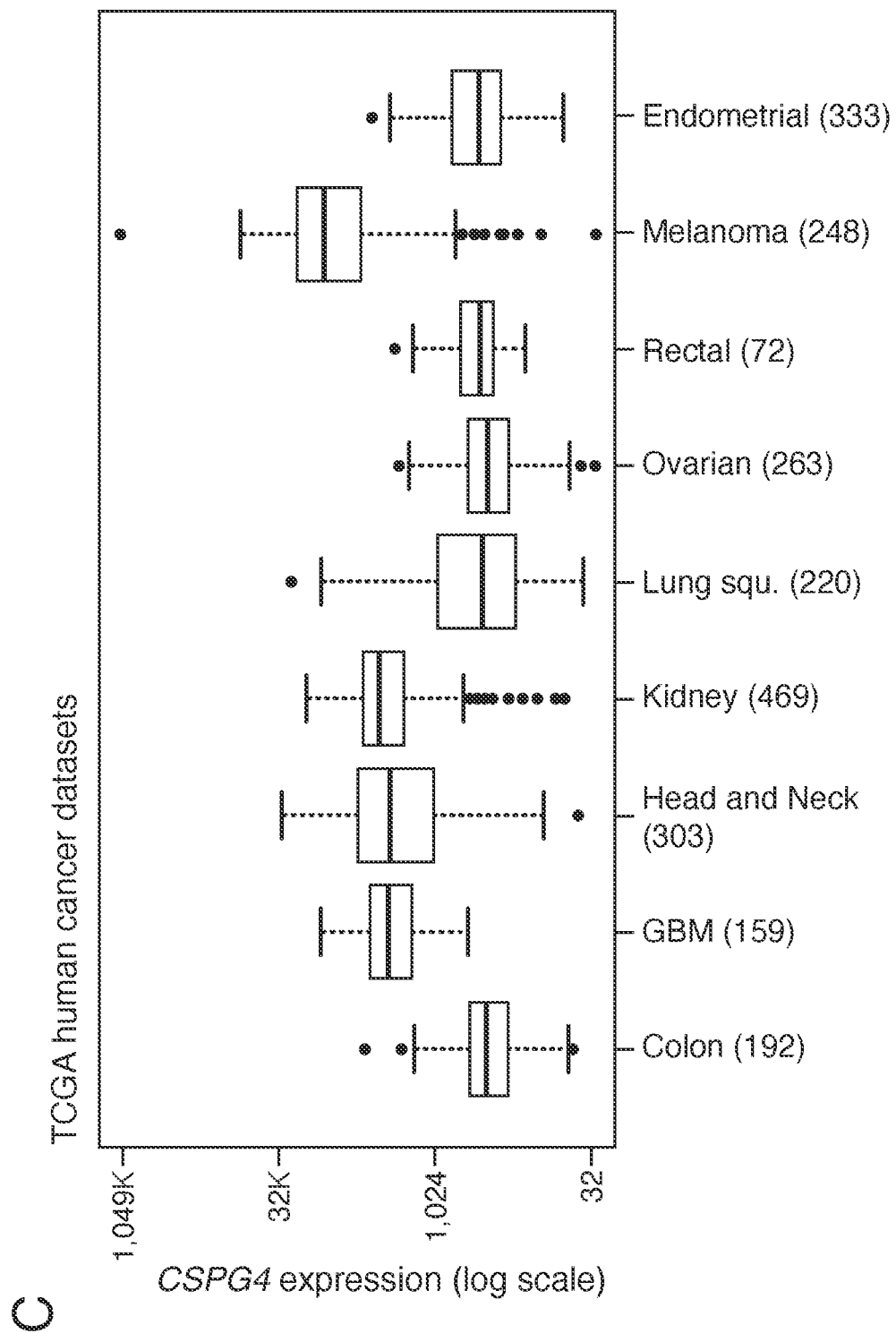
Figure 1:
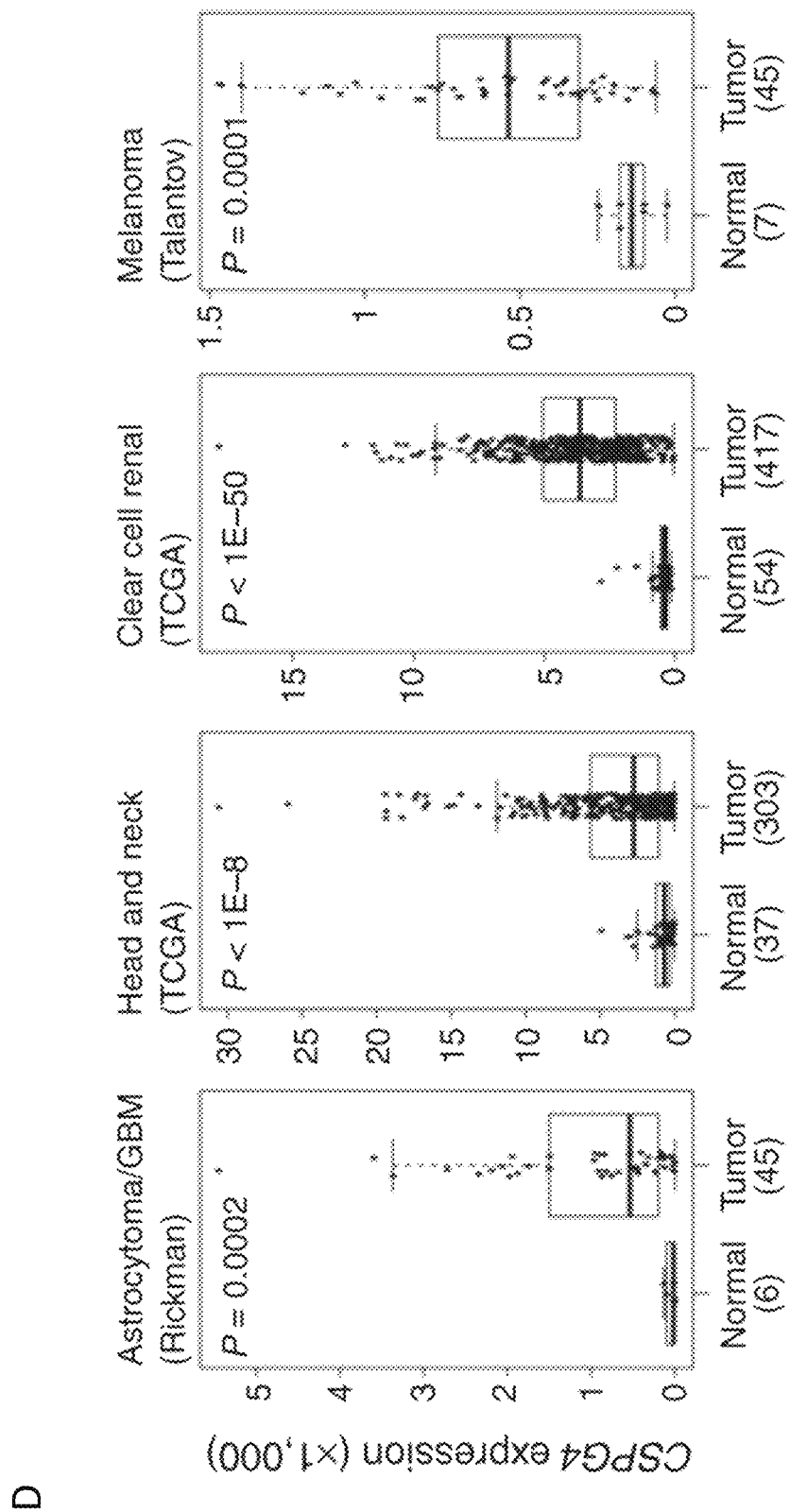
Figure 1:
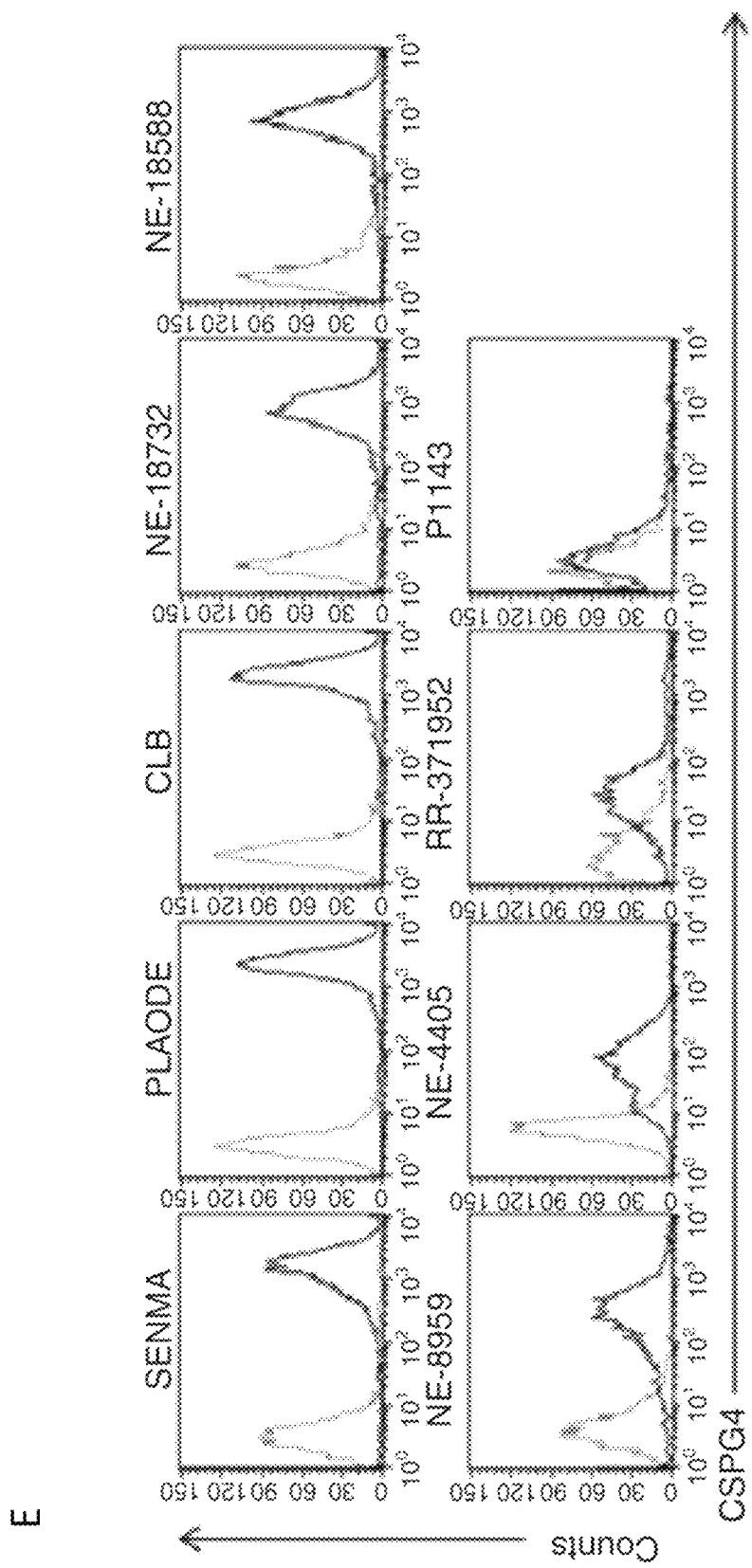
Figure 1:
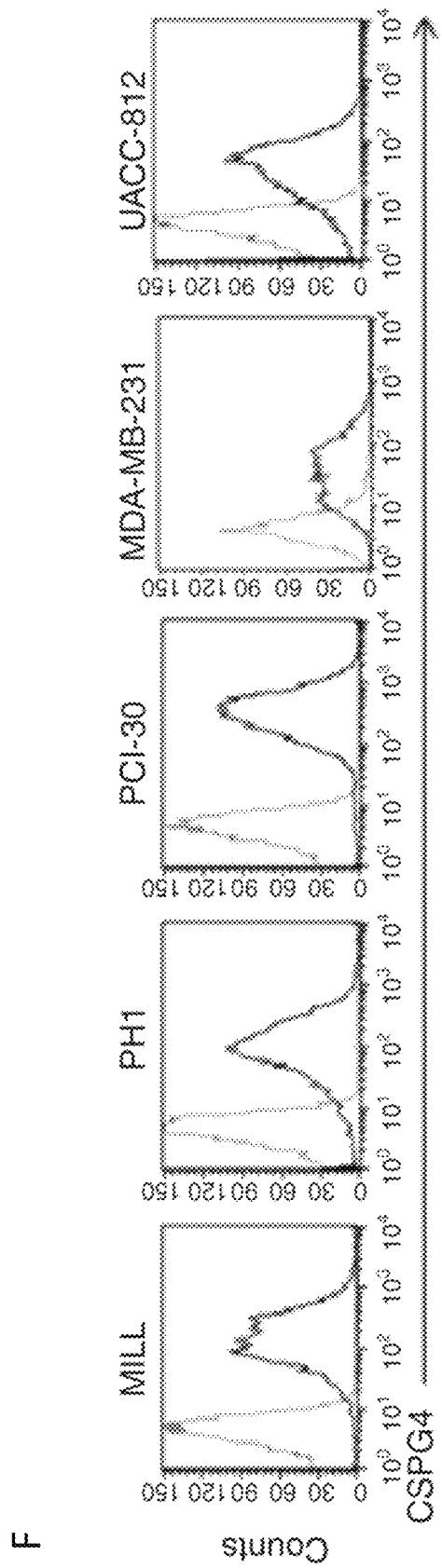

As CSPG4 was originally identified as a melanoma associated antigen, its expression was first independently validated using IHC in a melanoma tissue array containing multiple primary cutaneous and visceral melanomas and metastatic lesions. Examples of either strong or negative/low staining are shown in FIG. 1A. Consistent expression of the antigen was documented in all types of lesions, regardless of their primary or metastatic origin, or their cutaneous and visceral source. Melanomas were therefore analyzed as a whole group. Overall, 59% of melanomas showed strong staining and 25% displayed moderate staining (FIG. 1B).

The analysis was extended to include multiple samples of additional solid tumors including breast cancer, HNSCC, neuroblastoma, and mesothelioma. For the breast cancer array, staining was seen in invasive ductal and lobular carcinomas as well as in the small number of Paget's disease and ductal in situ carcinoma cases present on the array. Staining for representative invasive ductal carcinomas (either strong or negative/low) are shown in FIG. 1A and summarized in FIG. 1B, while other lesions were not sufficient in number for a comparative analysis. Staining for CSPG4 in invasive ductal carcinoma was remarkable with 77% of cases showing moderate or strong staining. HNSCC most predominantly (50%) expressed moderate staining for CSPG4, with only 20% showing strong staining. Although neuroblastoma exhibited the weakest overall staining, there was still a fraction of cases with moderate to strong expression. Finally, despite the limited number of mesotheliomas, these lesions all consistently expressed CSPG4. In certain embodiments it was considered that, at the protein level, all these malignancies exhibited variable but in most cases significant expression of CSPG4. To examine the expression of CSPG4 in a broader array of tumors publically available databases were examined for mRNA expression data. As shown in FIG. 1C, examination of TCGA datasets showed over expression of CSPG4 transcripts in melanoma and in glioma as anticipated based on the previously reported expression of the protein. Concordant with the protein expression data, CSPG4 mRNA expression was increased in HNSCC. Increased mRNA expression in clear cell renal carcinomas by in silico analysis, and overall, despite some intratumor variability, significant increased mRNA levels in all these tumor types relative to the corresponding normal tissues (FIG. 1D). Examination of the large Bittner multicancer dataset (www.oncomine.org) confirmed high CSPG4 mRNA expression in melanoma, clear cell renal carcinoma, HNSCC, multiple sarcoma types (chondrosarcoma, leiomyosarcoma, liposarcoma), gastrointestinal stromal tumors, skin, and vulvar squamous cell carcinomas. Of note several sarcoma cell lines have been previously reported to express CSPG4 protein. A number of other common malignancies such as colorectal, ovarian, and endometrial carcinoma did not show increased CSPG4 transcripts, consistent with the mRNA expression from the TCGA data sets. CSPG4 protein expression in an array of normal tissues was negative (FIG. 6). In addition to the normal tissues represented in FIG. 7, CSPG4 expression was evaluated on a total of 33 different types of tissues, all of which were negative. Using the public Novartis GeneAtlas (http://biogps.org) and TCGA databases, CSPG4 mRNA expression was observed in a number of normal tissues. However, the levels of expression are remarkably lower than those of cancer tissues (FIG. 7).

CSPG4 expression was examined in a series of cell lines from a variety of tumor types analyzed above. Expression of CSPG4 was detected in 8 of the 9 melanoma cell lines screened (FIG. 1E). Importantly, CSPG4 was detected on tumor cell lines representative of the above identified solid tumors such as mesothelioma (MILL and PHI), HNSCC (PCI-30) and breast cancer [MDA-MB-231 (adenocarcinoma) and UACC-812 (ductal carcinoma)] (FIG. 1F) all consistent with analysis of human tumor samples.

Example 4

Figure 2:
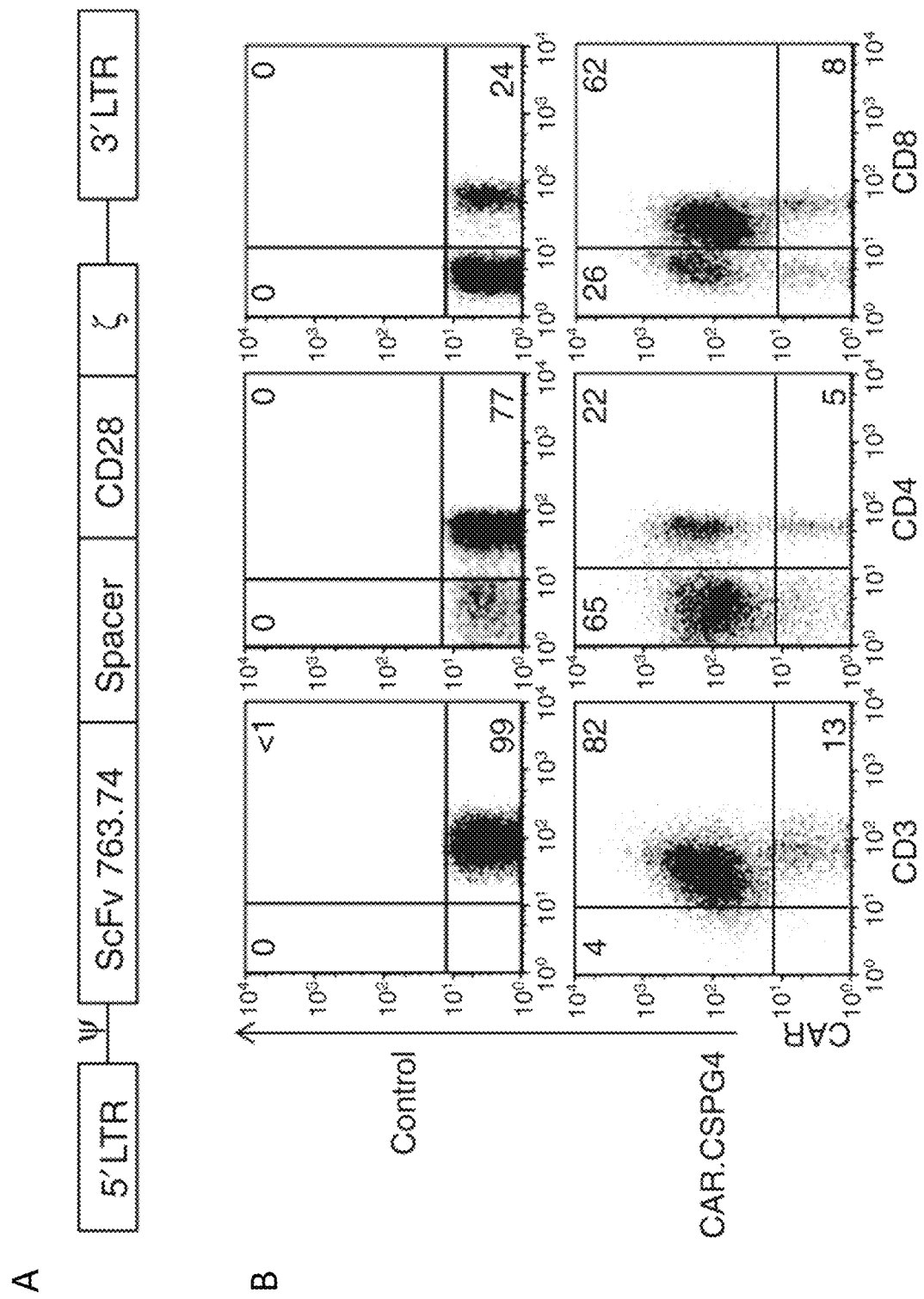
FIG. 2. Expression and function of CAR.CSPG4 in T cells. Panel A. Schematic representation of a retroviral vector encoding an example of a CSPG4-specific CAR. The CAR incorporates the CD28 costimulatory endodomain.
Figure 2:
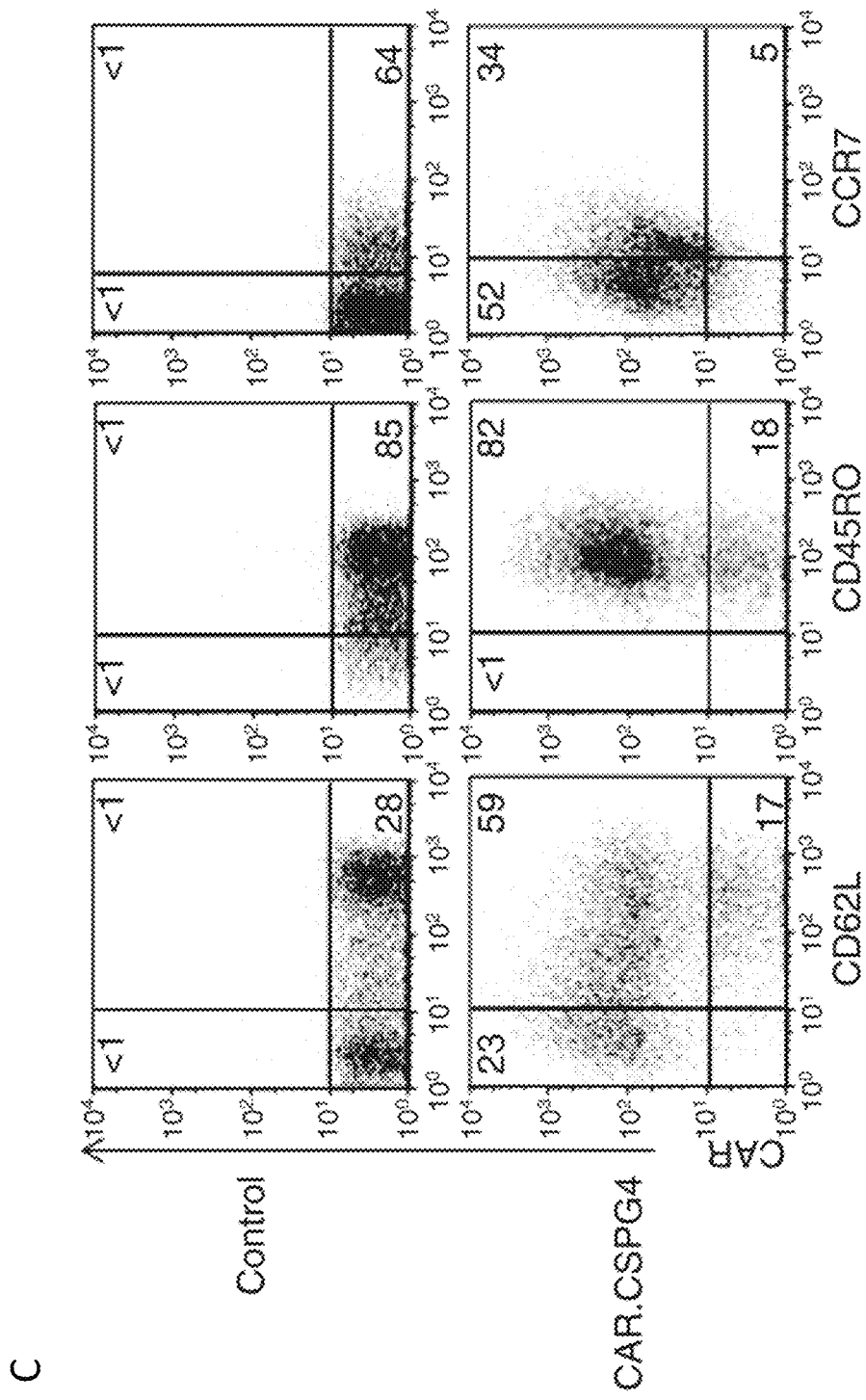

T Lymphocytes Expressing the CSPG4-Specific Car are Cytotoxic Against CSPG4+ Tumor Cell Lines but not Against Primary Normal Tissues To target CSPG4$^+$ tumors, a CSPG4-specific CAR was generated containing the CD28 costimulatory endodomain (CAR.CSPG4) (FIG. 2A). T lymphocytes from 4 healthy donors were engineered to express the CAR.CSPG4 using a gamma retroviral vector. Transduction efficiency was 80%±3%, and both CD4 and CD8 T cells stably expressed the CAR (26%±9% and 51%±16%, respectively), as assessed by phenotypic analysis by day 7 of culture (FIG. 2B). The majority of CAR.CSPG4+ T cells were CD45RO+ (76%±7%) and a fraction retained CD62L expression (51%±7%) and CCR7 (13%±2%), indicating that they were mainly composed of effector-memory T cells (FIG. 2C). The expression of CAR.CSPG4 by T cells was comparable to that obtained with a previously described CD19-specific CAR (CAR.CD19) (FIG. 9), which was used as an irrelevant-CAR control population.

Cytotoxic activity of control and CAR.CSPG4$^+$ T cells, after 1-2 weeks of culture, was assessed against K562, to measure natural killer cell-mediated activity, and against the melanoma derived cells lines P1143 (as CSPG4$^-$ target) and SENMA (as CSPG4+ target) (FIG. 1E) at various E:T ratios (FIG. 3A). CAR.CSPG4$^+$ but not control T lymphocytes significantly lysed the CSPG4$^+$ target (59%±5% vs. 11%±8% at 20:1 ratio)(p<0.01), while both CAR.CSPG4$^+$ and control T cells showed minimal activity against K562 (12%±9% vs. 13%±11%) and the CSPG4-target (<10% in both cases). The antitumor activity of CAR.CSPG4$^+$ T lymphocytes was also evaluated in a 72 hour co-culture assay (FIGS. 3B and C). CAR.CSPG4$^+$ and control T lymphocytes were co-cultured with GFP-expressing tumor cell lines at an E:T ratio ranging from 5:1 to 3:1 according to the kinetic growth of each cell line. CAR.CSPG4$^+$ T cells significantly controlled the growth of all CSPG4$^+$ cell lines tested: SENMA (residual tumor cells=0.1%±0.06%), CLB (0.1%±0.1%), UACC-812 (6%±6%), MILL (3%±5%), MDA-MB-231 (3%±3%), PHI (4%±3%), and PCI-30 (0.5%±0.5%), but not of the CSPG4− target P1143 (residual tumor cells 38%±10%). As expected, all tumor cell lines tested rapidly grow in the presence of control T lymphocytes (residual tumor cells for: SENMA=62%±3%, CLB=70%±6%, UACC-812=47%±15%, MILL=50%±8%, MDA-MB-231=42%±11%, PHI=29%±6%, PCI-30=17%±3%, and P1143=45%±10%). In all cases, the effects of CAR.CSPG4$^+$ T cells were significantly greater than those of control T cells (from p<0.05 to p<0.001). T cells expressing the control CAR.CD19 showed cytotoxic activity neither against CSPG4$^+$ nor CSPG4$^-$ targets (FIG. 8). As illustrated in FIG. 3, commercially available primary normal epithelial cell lines (small airway, kidney and prostate) derived from tissues found to express low levels of CSPG4 mRNA (FIG. 7) did not express detectable levels of the protein by flow cytometry (FIG. 3D), and were not lysed by CAR.CSPG4$^+$ T cells when tested in $^{51}$Cr release assays (FIG. 3E).

Example 5

CAR.CSPG4+ T Lymphocytes Secrete Th1 Cytokines and Proliferate in Response to CSPG4+ Tumors Because CAR.CSPG4 contains the CD28 costimulatory endodomain, CAR.CSPG4+ T lymphocyte proliferation was studied in response to CSPG4$^+$ tumor cells using a CFSE dilution assay. When CFSE-labeled control and CAR.CSPG4$^+$ T cells were cultured with irradiated SENMA tumor cells for 96 hours, a significant CFSE dilution occurred for CAR.CSPG4$^+$ T cells, with both CD4 and CD8 T cells proliferating at a higher percentage (66%±12% and 68%±8%, respectively) compared to control CD4 and CD8 T cells (8%±7% and 14%±10%, respectively) (p<0.05 and p<0.01, respectively) (FIGS. 4A and B). T cells transduced with the control CAR.CD19 also containing the CD28 endodomain did not show significant proliferation in response to CSPG4⁺ targets (FIG. 8). It was evaluated whether the inclusion of a "late" co-stimulatory endodomain, such as 4-1BB, in addition to CD28 (third generation construct) provided these T cells with additional proliferative and cytotoxic activity, but found no further benefits (FIG. 9).

The IL-2 and IFNγ cytokines released in response to the antigen was quantified by co-culturing control and CAR.CSPG4⁺ T lymphocytes with CSPG4⁺ or CSPG4⁻ tumor cells. As expected CAR.CSPG4⁺ T lymphocytes secreted significantly more IL-2 than control T cells only tail vein injection with either control or CAR.CSPG4⁺ T lymphocytes, and tumor growth quantified by sequential tumor volume measurements. In all three models, CAR.CSPG4⁺ T lymphocytes inhibited tumor growth significantly better than control T lymphocytes (FIG. 5). By day 30, melanoma tumors reached a volume of 879 mm$^3$±124 mm$^3$ in mice receiving CAR.CSPG4⁺ T lymphocytes versus 8359 mm$^3$±958 mm$^3$ in mice receiving control T cells (p<0.001) (FIG. 5A), and this corresponded to improved overall survival (FIG. 10). Although HNSCC and breast carcinoma tumors were not as aggressive as melanoma in vivo, in both models CAR.CSPG4⁺ T lymphocytes controlled tumor growth. By day 30 the size of HNSCC tumors was 19 mm$^3$±10 mm$^3$ in treated mice versus 190 mm$^3$±75 mm$^3$ in control mice (p<0.001) (FIG. 5B) and the size of breast carcinoma tumors was 28 mm$^3$±13 mm$^3$ in treated mice versus 166 mm$^3$±64 mm$^3$ in control mice (p<0.001) (FIG. 5C).

Example 6

Significance of Certain Embodiments

The involvement in several signaling pathways associated with cell proliferation, survival, migration, and suggested high expression in various types of cancers highlight the critical role that CSPG4 has in promoting tumor growth and simultaneously make it an attractive target for immunotherapy. By IHC, CSPG4 protein expression was independently validated in several solid tumors with poor prognosis, such as melanoma, breast cancer, mesothelioma and HNSCC. In silico analysis of microarray expression data confirmed overexpression of CSPG4 in tumors that were validated by IHC as compared to normal tissues, and also disclosed CSPG4 overexpression in other important malignancies including glioblastoma, clear cell renal carcinoma and sarcomas indicating that targeting this antigen has a major impact on a broad array of solid tumors, in at least particular cases.

Because CSPG4-specific mAbs can control tumor growth of CSPG4⁺ tumor cells in both melanoma and breast cancer tumor models, it was considered to improve the therapeutic benefits of this antibody-based approach by generating a CAR that targets the CSPG4 molecule. In contrast to mAb-based therapy, CAR-T cells should produce long-lasting effects, as engineered T cells can expand at the tumor site upon antigen stimulation if an appropriate co-stimulatory endodomain, derived from CD28, CD137 or CD134, is incorporated within the CAR. In contrast to a previous report, the CSPG4-specific CAR obtained from the same 763.74 single chain has potent antitumor activity. These striking differences were traced to two critical components introduced in the construct. First, the scFv in the CAR is coupled with the CD3-t endodomain of the TCR rather than the FcεRI-γ chain, which is known to promote a much weaker and less durable signaling. Second, the CD28 costimulatory endodomain was incorporated within the CAR to accomplish sustained IL-2 production and proliferation in response to CSPG4⁺ tumor cells, thus recapitulating previous observations for other CAR molecules. Of note, the inclusion of a second costimulatory endodomain derived from CD137 did not further improve the function of the CAR in vitro.

A significant improvement in the field by this work is the applicability of CAR.CSPG4⁺ T cells not only to target melanoma, but more broadly to other solid tumors generally characterized by poor prognosis with conventional treatments such as breast carcinoma, HNSCC and mesothelioma. It was demonstrated herein that CAR.CSPG4⁺ T cells produce IFNγ and promote tumor elimination not only when challenged with tumor cells with high CSPG4 expression but also with tumor cell lines characterized by moderate/low CSPG4 expression, such as the breast carcinoma tumor cell lines UACC-812 and MBA-MB-231. This further supports the advantages of antibody specificity coupled with the T-cell effector function, as mastered by CAR-modified T cells, which can target tumors neglected by naked corresponding antibodies due to the suboptimal expression of the targeted antigen.

Antitumor effects mediated by CAR.CSPG4+ T cells significantly limit tumor growth in xenograft mouse models of melanoma, HNSCC and breast carcinoma, strongly validating the in vitro findings. The lack of sustained and complete tumor eradication in these models was not caused by selection of CSPG4-negative tumor cells, as harvested tumors retained the expression of the antigen (FIG. 10), but conversely are likely to be attributed to an intrinsic limitation of the models, as T cells do not persist long term in these immunodeficient mice (FIG. 10).

To fully translate this approach, the differential expression of CSPG4 in tumor cells versus normal tissues is addressed in order to limit potential toxicities. The expression of CSPG4 was absent or negligible in normal tissue arrays as assessed by IHC. The analysis of publically available data sets indicates that there is some level of CSPG4 mRNA expression in several normal tissues. However, when one compared normal tissues with cancer tissues, the cancers show consistent and dramatically higher expression of CSPG4 at mRNA levels, and the in vitro analyses illustrate that primary epithelial cells derived from some of these tissues do not express significant amount of the protein and are not targeted by CAR.CSPG4+ T cells. Even though the tissue screening, bioinformatics analysis and lack of toxicity by in vitro experiments support the relevance of CSGP4 as a targetable antigen in cancer patients, in some cases the low levels of mRNA in normal tissues, as reported in public data sets, may promote sufficient protein expression in specific physiological conditions to become a target for CSPG4-specific CAR-T cells. Thus, in some embodiments, the inclusion of a suicide gene within the vector cassette is useful to allow the rapid elimination of CAR-modified T cells in case of undesired toxicity.

In summary, ample data is provided to support the use of CAR.CSPG4⁺ T cells to treat a broad range of solid CSPG4⁺ tumors for which the prognosis remains poor with conventional treatments. The combination of this approach with other biological agents further increases their activity and thus clinical benefits, in at least specific embodiments.

Although the present invention and its advantages have been described in detail, it should be understood that various changes, substitutions and alterations can be made herein without departing from the spirit and scope of the invention as defined by the appended claims. Moreover, the scope of the present application is not intended to be limited to the particular embodiments of the process, machine, manufacture, composition of matter, means, methods and steps described in the specification. As one of ordinary skill in the art will readily appreciate from the disclosure of the present invention, processes, machines, manufacture, compositions of matter, means, methods, or steps, presently existing or later to be developed that perform substantially the same function or achieve substantially the same result as the corresponding embodiments described herein may be utilized according to the present invention. Accordingly, the appended claims are intended to include within their scope such processes, machines, manufacture, compositions of matter, means, methods, or steps.

What is claimed is:

1. A method of inhibiting proliferation of cancer cells, comprising the step of contacting the cancer cells with a therapeutically effective amount of immune cells that express a chimeric antigen receptor (CAR) comprising scFv 763.74 that targets chondroitin sulfate proteoglycan-4 (CSPG4), wherein the cancer is glioblastoma.

2. The method of claim 1, wherein said contacting is performed in vitro.

3. The method of claim 1, wherein said contacting is performed in cell culture.

4. The method of claim 1, wherein said contacting is performed in vivo, and said immune cells are cells in an individual.

5. The method of claim 1, wherein said contacting is performed in vivo, and said immune cells are T cells in an individual.

6. The method of claim 3, wherein said immune cells are autologous to the individual.

7. The method of claim 3, wherein said immune cells are allogeneic to the individual.

8. The method of claim 1, wherein said immune cells are T cells, NK cells, dendritic cells, or a mixture thereof.

9. The method of claim 1, wherein said immune cells are T cells.

10. The method of claim 8, wherein said T cells are CD4+ T cells.

11. The method of claim 8, wherein said T cells are CD8+ T cells.

12. The method of claim 8, wherein said T cells are Treg cells.

13. The method of claim 1, wherein the CAR comprises a transmembrane domain selected from the group consisting of CD3-zeta, CD28, CD8a, CD4, or a combination thereof.

14. The method of claim 1, wherein the CAR comprises a co-stimulatory molecule endodomain selected from the group consisting of CD28, CD27, 4-IBB, OX40 ICOS, and a combination thereof.

15. The method of claim 2, wherein the individual has received, is receiving, or will receive an additional cancer treatment.

16. The method of claim 15, wherein the additional cancer treatment comprises chemotherapy, immunotherapy, radiation, surgery, hormone therapy, or a combination thereof.

17. The method of claim 1, wherein the immune cells harbor a polynucleotide that encodes the CAR.

18. The method of claim 17, wherein the polynucleotide further comprises a suicide gene.

* * * * *